(12) United States Patent
Blaner et al.

(10) Patent No.: US 6,171,837 B1
(45) Date of Patent: Jan. 9, 2001

(54) MOUSE AND HUMAN 9-CIS-RETINOL DEHYDROGENASE

(75) Inventors: William S. Blaner, New York, NY (US); Roseann Piantedosi Zott, River Edge, NJ (US); Mary V. Gamble; James R. Mertz, both of New York, NY (US)

(73) Assignee: The Trustees of Columbia University in the City of New York, New York, NY (US)

( * ) Notice: Under 35 U.S.C. 154(b), the term of this patent shall be extended for 0 days.

(21) Appl. No.: 08/940,424

(22) Filed: Sep. 29, 1997

(51) Int. Cl.$^7$ .............................. C12N 9/04; C07H 21/04
(52) U.S. Cl. ........................................ 435/190; 536/23.2
(58) Field of Search .................... 435/190, 26; 536/23.2; 530/412

(56) References Cited

PUBLICATIONS

Blaner, W. S. and Olson, J. A. (1994) The Retinoids, Biology, Chemistry, and Medicine (Sporn, M. B. et al., eds.), 229–255, Raven Press, New York. (Exhibit 1).

Boerman, M. H. E. M. and Napoli, J. L. (1995) "Effects Of Sulfhydryl Reagents, Retinoids, and Solubilization On The Activity Of Microsomal Retinol Dehydrogenase," *Arch. Biochem. Biophys.* 321:434–441. (Exhibit 2).

Boerman, M. H. E. M. and Napoli, J. L.(1995) "Characterization Of A Microsomal Retinol Dehydrogenase: A Short–Chain Alcohol Dehydrogenase With Integral And Peripheral Membrane Forms That Interacts With Holo–CRBP (Type I), " *Biochemistry* 34:7027–7037. (Exhibit 3).

Boleda, M. D. et al. (1993) "Physiological Substrates For Alcohol Dehydrogense Classes: Aldehydes Of Lipid Peroxidation ω–Hydroxyfatty Acids, And Retinoids," *Arch. Biochem. Biophys.* 307:85–90. (Exhibit 4).

Chai, X. et al. (1995) "Cloning Of A cDNA For A Second Retinol Dehydrogenase Type II, " *J. Biol. Chem.* 270:28408–28412. (Exhibit 5).

Driessen, C. A. et al. (1995) "Cloning And Expression of a cDNA Encoding Bovine Retinal Pigment Epithelial 11–cis Retinol Dehydrogenase," *Invest. Ophthalmol. & Visual Sci.* 36, 1988–1996. (Exhibit 6).

Duester, G. (1996) "Involvement Of Alcohol Dehydrogenase, Short–Chain Dehydrogenase/Reductase, Aldehyde Dehydrogenase, and Cytochrome P450 in the Control of Retinoid Signaling by Activation of Retinoic Acid Synthesis," *Biochemistry* 35:12221–12225. (Exhibit 7).

El Akawi, Z. and Napoli, J. L. (1994) "Rat Liver Cytosolic Retinal Dehydrogenase: Comparison of 13–cis, 9–cis, and all–trans–Retinal as Substrates and Effects of Cellular Retinoid–Binding Proteins," *Biochemistry* 33:1938–1943. (Exhibit 8).

Hebuterne, X. et al. (1995) "Intestinal Absorption and Metabolism of 9–cis–β–carotene In Vivo: Biosynthesis Of 9–cis–retinoic Acid," *J. Lipid Res.* 36:1264–1273. (Exhibit 9).

(List continued on next page.)

Primary Examiner—Christopher S. F. Low
Assistant Examiner—Devesh Srivastava
(74) Attorney, Agent, or Firm—John P. White; Cooper & Dunham LLP

(57) ABSTRACT

This invention provides an isolated nucleic acid molecule (SEQ ID NO:1) encoding a human 9-cis-retinol dehydrogenase. Also provided is a 9-cis-retinol dehydrogenase encoded by the isolated nucleic acid molecule, wherein the 9-cis-retinol dehydrogenase comprises the amino acid sequence of SEQ. ID NO: 2. This invention also provides isolated nucleic acid molecules comprising the nucleotide sequence shown in any of SEQ. ID NOS: 6, 7, and 8 encoding mouse 9-cis-retinol dehydrogenases.

3 Claims, 12 Drawing Sheets

```
GAGACTGGGAGCAGTCTCTTAAACAAAAGCAAAAGAATAAGCTTCGGGCGCTGTAGTACCTGCCAGCTTT    70
CGGCACAGGAGGCTGCCAGCCTGTAGGTGACTTGGGCTCCAGCTATGTGGCTGCCTGTTCTGCTGGGTGCC  140
TTACTCTGGGCAGTGCTGTCGTTGCTCACGGACCGGCAGANCCTGCCCGCCAGCAATGCCTTTGTCTTCA  210
TCACCGGCTGTGACTCAGGCTTTGGGCGCCTTCTGGCACTGCAGCTGGACCAGAAAAGCTTCCCANTCCT   280
GGCCAGCTGCCTCACCCCCTCCGGGGCCGAGGACCTGCAGGGGGTGGCTTCTTCCGGCTTCAACACCACC   350
NTCTTGGATATCACTGATCGCCAGAGCTTCCAGCAGGCAGCCAAGTGGGTGGAGATGCACGTTAAGCAAG   420
CAGGGCTTTTTGGTCTCGTGAATAATGCTGGTGTGGCTGGTATCATCGGACCCACACCATGGCTGACCCG   490
GGACGATTTCCAGCGGGTGCTGAATCTGAACACAATGGGTCCCATCGGCGTCACCCTTGCCCTGCTGCCT   560
CTGCTGCAGCCAAGCCCGGGCCCGGGTGATCAACATCACCAGCCGTGCTGGGTCGCCTGGCAGCCAATGCTG   630
GGGGCTACTGTGTCTCCAAATTTGGCCTGCAGGCCTTCTCTGACAGCCTGAGGCGGGATGTAGCTCATTT   700
TGCCATACGGAGTCCATNGTGGAGCGCTGGTTTNTTCCGAACCCCTGTGACCAACTTGGAGAGTNTGGAG   770
AAAACCCTGCAGGCCTGCTGGGCACGCCTGCCTCCTGCCACACAGGCCCACTATGGGGGCGCCTTCCTCA   840
CCAACTACCTGAAAATGCAACAGCGGCATCATGAACCTGATCTGTCACCCGGACCTAACCAAGGTGAGCCG   910
ATGCCTGCACCATGCCCTGACTGCTCGACACCCCCGAACCCCGCTACAGCCCAGGTTGGGATGCCAAGCTG   980
CTCTCGCTGCCTGCCTCCTACCCTGCCCAGCCAGCCTGGTGGATGCTGTGCTCACCTGGGTGCCTTCCCAAGC   1050
CTGCCCAAGCAGTCTACTGAATCCACGCCTTCCAGCAAGAGATTGTTTTTCAAGGACAAGGACTTTGATTT  1120
ATTTCTGCCCCCACCCTGGTACTGCCTGGCTGGCTGCCTGCCACAAAATAAGCACTAACAAAAGTGTATTGTTTA 1190
AAAAATAAAAAGAAGGTGGGCAGAAATGTGCCCACTGGAA 1230
```

OTHER PUBLICATIONS

Labrecque, J. et al. (1993) "Purification and Partial Characterization of a Rat Kidney Aldehyde Dehydrogenase that Oxidizes Retinal to Retinoic Acid," *Biochem. Cell Biol.* 71:85–89. (Exhibit 10).

Labrecque, J. et al. (1995) "A Novel Isoenzyme of Aldehyde Dehydrogenase Specifically Involved in the Biosynthesis of 9–cis and 11–trans Retinoic Acid," *Biochem. J.* 305:681–684 (Exhibit 11).

Napoli, J. (1996) "Retinoic Acid Biosynthesis and Metabolism," *FASEB J.* 10:993–1001. (Exhibit 12).

Simon, A. et al. (1995) "The Retinal Pigment Epithelial–specific 11–cis Retinol Dehydrogenase Belongs to the Family of Short Chain Alcohol Dehydrogenase," *J. Biol. Chem.* 270: 1107–1112. (Exhibit 13).

Mertz, et al. (1997) "Identification and Characterization of A Sterospecific Human Enzyme That Catalyzes 9–cis–Retinol Oxidation," *J. Biol. Chem.* 272(18):11744–11749 (Exhibit 1).

FIG. 1A

| | |
|---|---|
| GAGACTGGGACCAGTCTCTTAAACAAAGAATAAGCTTCGGGGGCTGTAGTACCTGCCAGCTTT | 70 |
| CGCCACAGGAGGGTGCCACCTGTAGGTCACTTGGGCTCCAGCTATGTGGCTGCCTCTCTGCTGGGTGCC | 140 |
| TTACTCTGGGCAGTCTGTGGTTGCTCAGGGACCGGCAGANCCTGCCGGCCAGCAATGCCTTTGTCTTCA | 210 |
| TCACCGGCTCTGACTCAGGCTTTGGGCCCCTTCTGCACTCAGCTGACCAGAAAAGCTTCCGANTCCT | 280 |
| GGCCAGCTGCCTGACCCCTCCGGGGCGGAGGACCTGCAGGGGTGCCTTCTTCCGGCTTCAACACCACC | 350 |
| NTGTTGGATATCACTGATCCCCAGAGCTTCCAGCAGGCAGCCAAGTGGGTGCGAGATGCACGTTAAGGAAG | 420 |
| CAGGGCTTTTGGTCTCGTGAATAATGCTGGCTGTATCATCGGACCCACACCATGGCTGACCCG | 490 |
| GGACGATTTCCAGCGGGTGCTGAATGCAACACAATGGTCCCATGGGGTCACCCTTGCCCTGCCCT | 560 |
| CTGCTCAGCAAGCCCGGGTGATCAACATCACCAGCGTCTGGTCCCTGGCCAGCCAATGTG | 630 |
| GGGGCTACTGTCTCTCCAAATTTGGCCTGAGGCCTTCTCTGACAGCCTGAGGCGGATGTAGCTCATTT | 700 |
| TGGGATACGGGAGTCCATNGTGGGAGCCTGTGTTNTTCCGAACCCCTGTGACCAACTTGAGAGTNTGGAG | 770 |
| AAAACCCTGCAGGCCTGCTCGGGCAGGCTGCCTCCTGCCACACAGCCCACTATGGGGGGGCCTTCCTCA | 840 |
| CCAAGTACCTGAAAATGCAACAGGGCATCATGAACCTGATCTGTGACCCGGACCTAACCAAGGTGAGCCG | 910 |
| ATGCCTGAGCATGCCTGACTGCTCGACACCCCGAACCCGCTACAGCCCAGGTTGGATGCCAAGCTG | 980 |
| CTCTGGCTGCCTGCCTCCTACCTGCCAGCCAGCCTGTGATGCTGCTCACCTGGGTCCTTCCCAAGC | 1050 |
| CTGCCCAAGCAGTCTACTGAATCCAGCTTCCAGCAAGAGATTGTTTTCAAGGACAAGGACTTTGATTT | 1120 |
| ATTTCTGCCCCACCCTGGTACTGCCTGGTGCCTGCCACAAAATAAGCACTAACAAAAGTGTATTGTTTA | 1190 |
| AAAAATAAAAAGAAGTGGGCAGAAATGTGCCAGTGGAA 1230 | |

FIG. 1B

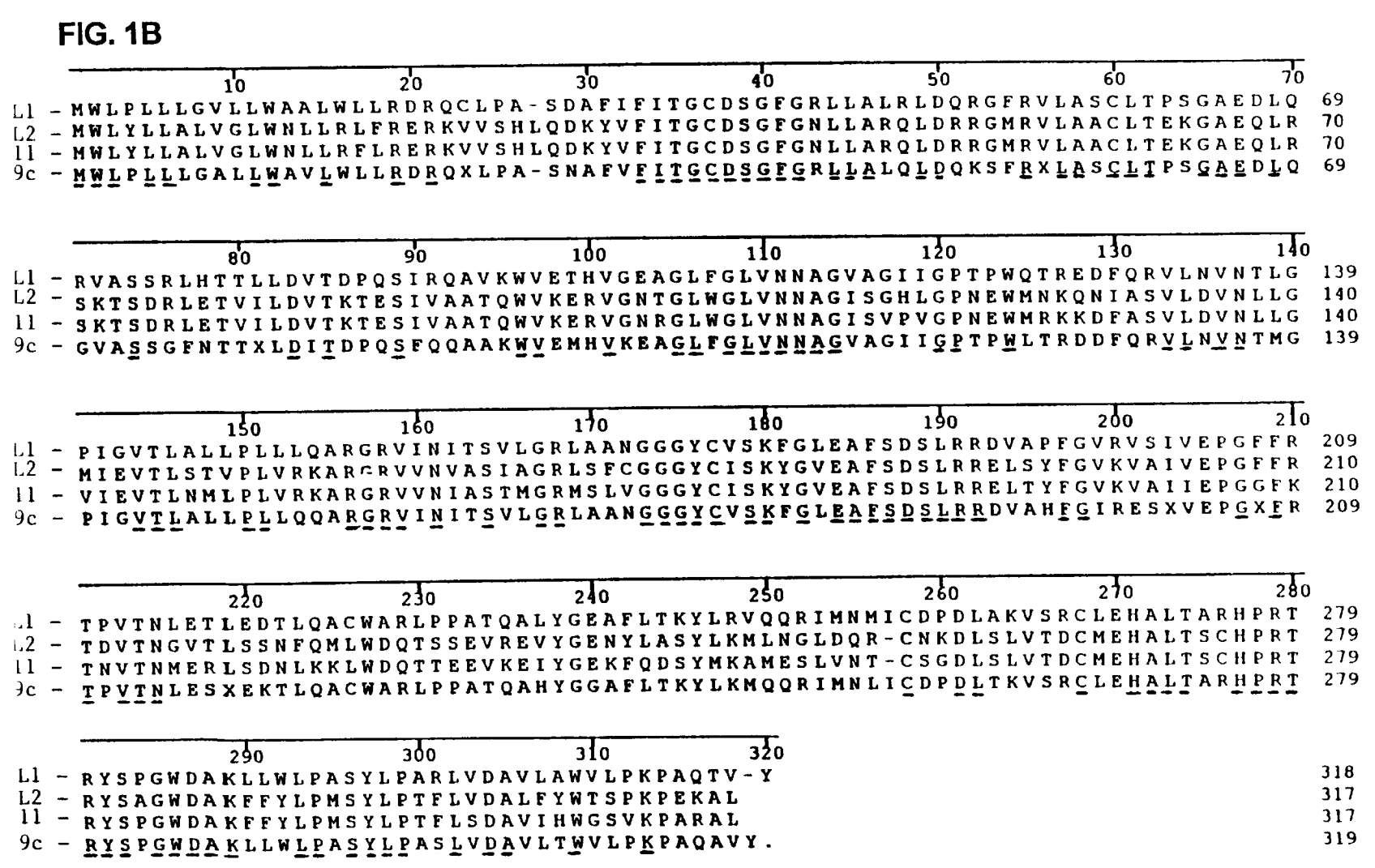

```
                        10         20         30         40         50         60         70
                        |          |          |          |          |          |          |
L1  - MWLPLLLGVLLLWAALWLLRDRQCLPA-SDAFIFITGCDSGFGRLLALRLDQRGFRVLASCLTPSGAEDLQ      69
L2  - MWLYLLALVGLWNLLRFRERKVVSHLQDKYVFITGCDSGFGNLLARQLDRRGMRVLAACLTEKGAEQLR        70
l1  - MWLYLLALVGLWNLLRFLRERKVVSHLQDKYVFITGCDSGFGNLLARQLDRRGMRVLAACLTEKGAEQLR        70
9c  - MWLPLLLGALLLWAVLWLLRDQXLPA-SNAFVFITGCDSGFGRLLALQLDQKSFRXLASCLTPSGAEDLQ        69

80         90        100        110        120        130        140
                        |          |          |          |          |          |          |
L1  - RVASSRLHTTLLDVTDPQSIRQAVKWVETHVGEAGLFGLVNNAGVAGIIGPTPWQTREDFQRVLNVNTLG      139
L2  - SKTSDRLETVILDVTKTESIVAATQWVKERVGNTGLWGLVNNAGISGHLGPNEWMNKQNIASVLDVNLLG      140
l1  - SKTSDRLETVILDVTKTESIVAATQWVKERVGNRGLWGLVNNAGISVPVGPNEWMRKKDFASVLDVNLLG      140
9c  - GVASSGFNTTXLDITDPQSFQQAAKWVEMHVKEAGLFGLVNNAGVAGIIGPTPWLTRDDFQRVLNVNTMG      139

150        160        170        180        190        200        210
                        |          |          |          |          |          |          |
L1  - PIGVTLALLPLLPLLQARGRVINITSVLGRLAANGGGYCVSKFGLEAFSDSLRRDVAPFGVRVSIVEPGFFR     209
L2  - MIEVTLSTVPLVRKARCRVVNVASIAGRLSFCGGGYCISKYGVEAFSDSLRRELSYFGVKVAIVEPGFFK     210
l1  - VIEVTLNMLPLVRKARGRVVNIASTMGRMSLVGGGYCISKYGVEAFSDSLRRELTYFGVKVAIIEPGGFK     210
9c  - PIGVTLALLPLLPLLQQARGRVINITSVLGRLAANGGGYCVSKFGLEAFSDSLRRDVAHEGIRESXVEPGXFR    209

220        230        240        250        260        270        280
                        |          |          |          |          |          |          |
L1  - TPVTNLETLEDTLQACWARLPPATQALYGEAFLTKYLRVQQRIMNMICDPDLAKVSRCLEHALTARHPRT     279
L2  - TDVTNGVTLSSNFQMLWDQTSSEVREVYGENYLASYLKMLNGLDQR-CNKDLSLVTDCMEHALTSCHPRT     279
l1  - TNVTNMERLSDNLKKLWDQTTEEVKEIYGEKFQDSYMKAMESLVNT-CSGDLSLVTDCMEHALTSCHPRT     279
9c  - TPVINLESXEKTLQACWARLPPATQAHYGGAFLTKYLKMQQRIMNLICDPDLTKVSRCLEHALTARHPRT     279

290        300        310        320
                        |          |          |          |
L1  - RYSPGWDAKLLWLPASYLPARLVDAVLAWVLPKPAQTV-Y                                   318
L2  - RYSAGWDAKFFYLPMSYLPTFLVDALFYWTSPKPEKAL                                     317
l1  - RYSPGWDAKFFYLPMSYLPTFLSDAVIHWGSVKPARAL                                     317
9c  - RYSPGWDAKLLWLPASYLPASLVDAVLTWVLPKPAQAVY.                                   319
```

FIG. 4A

```
                  XX-TXXXACXGGGGCTCGGA--GCCXXXAGXAXCXGCX-CXXGTXTGCTXX       15
NMKT7.SEQ         T-------GGCTCNGA--G------NCCACTAGTAACGGCCGCCAGTGTGCTGG       47
NMLRDH.SEQ        CT-TGGTACCGAGCTCGGA--NCCACTAGTAACGGCCGCCAGTGTGCTGG       47
PCRD4.SEQ         GAGTCACACAGGGATAGGTCTGCCCACAGGACCAGCT-CAGGTTTATTTC    49
                            10        20        30        40        50

XATTCGGXACXAXG---CTTXXCCATAXXXXXGT----------XTXXG--A   29
NMKT7.SEQ                                                                   
NMLRDH.SEQ        AATTCGGCACGAGG---CTTAGCTGTAGCTAGT----------GTGGG---A  83
PCRD4.SEQ         -ATTAGCTACAAAGTGCTTGCCCATAATCTGTTTCACACAATAAGCCATA    98
                            60        70        80        90       100

GCXTGXXAAXXCT----------AXGXXXXAXAGTCTC--XXXXAGCAGAC-AGAAA  40
NMKT7.SEQ         GANTCGG--------ACCATG--------------------AGCAGAC-AGAAA    125
NMLRDH.SEQ        AATTCGG--------CTTAGCTGTAGCTAGT-----AGGAGCAAAGTCTC--TCAAGCAGAC-AGAAA
PCRD4.SEQ         -ATTAGCTACAAAGTGCTTGCCCATAATCTGTTTCGCCAAGCATATAGTCTXATCTGCTCAGACCAGACA 148
                           110       120       130       140       150

NMKT7.SEQ         GCTACAGCTT--CACACATT--GTGTT---GCC---              67
NMLRDH.SEQ        GCTACAGCTT--CACACATT--GTGTT---GCC---T             152
PCRD4.SEQ         TTTCCAGCTAAGTGTTAGGGCCAAGGCTAAAGGGTAGAGGAAAT      198
                           160       170       180       190       200
```

NMKT7.SEQ Kid
NMLRDH.SEQ Liv
PCRD4.SEQ Tes

FIG. 4B

```
                           210                 220                 230                 240                 250
NMKT7.SEQ      GCCAGCTTTCCCCCAG--AGCCTAXGCTGCCCCTCAGCAGGGCATCTCATCC          115
NMLRDH.SEQ     GCCAGCTTTCCCCCAG--AGCCTAGGCTGCCCCTCAGCAGGGCATCTCATCC          195
PCRD4.SEQ      GACAAGTTTTCTGCCCCAGCCTAAGCTGCCCCTCAGCAGGGCATCTCATCC           248

260                 270                 280                 290                 300
NMKT7.SEQ      CATCATGTGGCTGCCCTCTGCCTTCTGGGTGCCTTGCTGTGGGCAGTGCTGT          165
NMLRDH.SEQ     CATCATGTGGCTGCCCTCTGCCTTCTGGGTGCCTTGCTGTGGGCAGTGCTGT          245
PCRD4.SEQ      CATCATGTGGCTGCCCTCTGCCTTCTGGGTGCCTTGCTGTGGGCAGTGCTGT          298

310                 320                 330                 340                 350
NMKT7.SEQ      GGTTGCTCAGAGACCGGCAGAGCCTGCCCGGCCAGTGATGCTTTTCATCTTC          215
NMLRDH.SEQ     GGTTGCTCAGAGACCGGCAGAGCCTGCCCGGCCAGTGATGCTTTTCATCTTC          295
PCRD4.SEQ      GGTTGCTCAGAGACCGGCAGAGCCTGCCCGGCCAGTGATGCTTTTCATCTTC          348

360                 370                 380                 390                 400
NMKT7.SEQ      ATCACTGGCTGTGACTCTGGCTTTGGGCCGCCTTCTGGCACTGCAACTTGA          265
NMLRDH.SEQ     ATCACTGGCTGTGACTCTGGCTTTGGGCCGCCTTCTGGCACTGCAACTTGA          345
PCRD4.SEQ      ATCACTGGCTGTGACTCTGGCTTTGGGCCGCCTTCTGGCACTGCAACTTGA          398
```

FIG. 4C

```
                                                                                               315
NMKT7.SEQ                       CCAGAAGGGCTTCCAAGTCCTGGCCGGCCTGACCCCCTCTGGAGCAG
NMLRDH.SEQ    CCAGAAGGGCTTCCAAGTCCTGGCCGGCCTGACCCCCTCTGGAGCAG  395
PCRD4.SEQ     CCAGAAGGGCTTCCAAGTCCTGGCCGGCCTGACCCCCTCTGGAGCAG  448
                       410       420       430       440      450

NMKT7.SEQ                       AAGACCTGCAGCAGATGGCCCTCCCCGCCTCCCACACAACACTGGAT  365
NMLRDH.SEQ    AAGACCTGCAGCAGATGGCCCTCCTCCCGCCTCCCACACAACACTACTGGAT  445
PCRD4.SEQ     AAGACCTGCAGCAGATGGCCCTCCTCCCGCCTCCCACACAACACTACTGGAT  498
                       460       470       480       490      500

NMKT7.SEQ                       ATCACTGATCCCCAGAATGTCCAGCAAGTTGCCAAGTGGGTGAAGACACG  415
NMLRDH.SEQ    ATCACTGATCCCCAGAATGTCCAGCAAGTTGCCAAGTGGGTGAAGACACG  495
PCRD4.SEQ     ATCACTGATCCCCAGAATGTCCAGCAAGTTGCCAAGTGGGTGAAGACACG  548
                       510       520       530       540      550

NMKT7.SEQ                       TGTTGGAGAAAACTGGACTTTTTGGTCTGGTGAATAACGCTGGCGTAGCTG  461
NMLRDH.SEQ    TGTTGGAGAAAACTGGACTTTTTGGTCTGGTGAATAACGCTGGCGTAGCTG  545
PCRD4.SEQ     TGTTGGAGAAAACTGGACTTTTTGGTCTGGTGAATAACGCTGGCGTAGCTG  598
                       560       570       580       590      600
```

FIG. 4D

```
              GTATCATCGGGCCCCACACCATGGCTAACACAGGATGATTTCCAGAGAGTA
NMKT7.SEQ                                                              461
NMLRDH.SEQ    GTATCATCGGGCCCCACACCATGGCTAACACAGGATGATTTCCAGAGAGTA  595
PCRD4.SEQ     GTATCATCGGGCCCCACACCATGGCTAACACAGGATGATTTCCAGAGAGTA  648
              610       620       630       640       650

CTGAGTGTGAACACACTGGGGCCCCATCGGTGTCACCCCTTGCCCTGCTGCC
NMKT7.SEQ                                                              461
NMLRDH.SEQ    CTGAGTGTGAACACACTGGGGCCCCATCGGTGTCACCCCTTGCCCTGCTGCC  645
PCRD4.SEQ     CTGAGTGTGAACACACTGGGGCCCCATCGGTGTCACCCCTTGCCCTGCTGCC  698
              660       670       680       690       700

CCTGCTACAGCAGGCCAGGGGTCGGGTGGTCAACATCACCAGTGTCTTGG
NMKT7.SEQ                                                              461
NMLRDH.SEQ    CCTGCTACAGCAGGCCAGGGGTCGGGTGGTCAACATCACCAGTGTCTTGG  695
PCRD4.SEQ     CCTGCTACAGCAGGCCAGGGGTCGGGTGGTCAACATCACCAGTGTCTTGG  748
              710       720       730       740       750

GCCGCATAGCCAGCCAATGGCGGGGGCTACTGTGTCTCCAAGTTTGGCCTG
NMKT7.SEQ                                                              461
NMLRDH.SEQ    GCCGCATAGCCAGCCAATGGCGGGGGCTACTGTGTCTCCAAGTTTGGCCTG  745
PCRD4.SEQ     GCCGCATAGCCAGCCAATGGCGGGGGCTACTGTGTCTCCAAGTTTGGCCTG  798
              760       770       780       790       800
```

FIG. 4E

```
NMKT7.SEQ                                                                                              461
NMLRDH.SEQ    GAGGCCTTCTCTGACAGCCTGAGGCGGGACATGGCTCCGTTCGGAGTACA                                       795
PCRD4.SEQ     GAGGCCTTCTCTGACAGCCTGAGGCGGGACATGGCTCCGTTCGGAGTACA                                       848
                       810           820           830           840           850

NMKT7.SEQ     AGTCTCCATTGTGGAGCCTGGCTTCTTTCGAACCCCTGTGACCAACCTGG                                       461
NMLRDH.SEQ    AGTCTCCATTGTGGAGCCTGGCTTCTTTCGAACCCCTGTGACCAACCTGG                                       845
PCRD4.SEQ     AGTCTCCATTGTGGAGCCTGGCTTCTTTCGAACCCCTGTGACCAACCTGG                                       898
                       860           870           880           890           900

NMKT7.SEQ                                                                                              461
NMLRDH.SEQ    AGAGTCTGGAGAGCACCCTGAAGGCTTGTTGGGCCCGGCTACCTCCAGCT                                       895
PCRD4.SEQ     AGAGTCTGGAGAGCACCCTGAAGGCTTGTTGGGCCCGGCTACCTCCAGCT                                       948
                       910           920           930           940           950

NMKT7.SEQ                                                                                              461
NMLRDH.SEQ    ATACAGGCCCACTACGGGGAAGCCTTCCTCGATACTTATCTTCGAGTACA                                       945
PCRD4.SEQ     ATACAGGCCCACTACGGGGAAGCCTTCCTCGATACTTATCTTCGAGTACA                                       998
                       960           970           980           990           1000
```

FIG. 4F

```
NMKT7.SEQ      ━━━━━━━━━━━━━━━━━━━━━━━━━━━━━━━━━━━━━━━━━━━━━━━━━━ 461
               GCGCCGCATCATGAACCTGATCTGTGACCCAGAACTAACGAAGGTGACCA 1050
                     1010      1020      1030      1040
NMLRDH.SEQ     GCGCCGCATCATGAACCTGATCTGTGACCCAGAACTAACGAAGGTGACCA 995
PCRD4.SEQ      GCGCCGCATCATGAACCTGATCTGTGACCCAGAACTAACGAAGGTGACCA 1048

NMKT7.SEQ      ━━━━━━━━━━━━━━━━━━━━━━━━━━━━━━━━━━━━━━━━━━━━━━━━━━ 461
               GCTGCCCTGGAGCATGCCXTGACTGCTCGCCACCCCGAACACGXTACAGC 1100
                     1060      1070      1080      1090
NMLRDH.SEQ     GCTGCCCTGGAGCATGCCCTGACTGCTCGCCACCCCGAACACGCTACAGC 1045
PCRD4.SEQ      GCTGCCCTGGAGCATGCCCTGACTGCTCGCCACCCCGAACACGTTACAGC 1098

NMKT7.SEQ      ━━━━━━━━━━━━━━━━━━━━━━━━━━━━━━━━━━━━━━━━━━━━━━━━━━ 461
               CCAGGCTGGGATGCCCAAGCTGCTCTGGCTGCCCTGCCCTACCTTCCAGC 1150
                     1110      1120      1130      1140
NMLRDH.SEQ     CCAGGCTGGGATGCCCAAGCTGCTCTGGCTGCCCTGCCCTACCTTCCAGC 1095
PCRD4.SEQ      CCAGGCTGGGATGCCCAAGCTGCTCTGGCTGCCCTGCCCTACCTTCCAGC 1148

NMKT7.SEQ      ━━━━━━━━━━━━━━━━━━━━━━━━━━━━━━━━━━━━━━━━━━━━━━━━━━ 461
               CAGGGTGGTGGATGCTGCTCACXTGGATCCTTCCCCGGCCCGCCCAGT 1200
                     1160      1170      1180      1190
NMLRDH.SEQ     CAGGGTGGTGGATGCTGTGCTCACCTGGATCCTCACCTTCCCCGGCCCGCCCAGT 1145
PCRD4.SEQ      CAGGGTGGTGGATGCTGTGCTCACCTGGATCCTCACCTTCCCCGGCCCGCCCAGT 1198
```

FIG. 4G

```
                 CAGTCTCCTGATTCCAGCTTTACAGCAAGAXGCTGATTTTGAAAAGCAAG
                          1210          1220          1230          1240          1250
NMKT7.SEQ                                                                              461
NMLRDH.SEQ       CAGTCTCCTGATTCCAGCTTTACAGCAAGAAGCTGATTTTGAAAAGCAAG    1195
PCRD4.SEQ        CAGTCTCCTGATTCCAGCTTTACAGCAAGAAGCTGATTTTGAAAAGCAAG    1248

GCATCTATTTCTGTGTCTACCCAGTGCCTGGTTTCTGATACCAATTA
                          1260          1270          1280          1290          1300
NMKT7.SEQ                                                                              461
NMLRDH.SEQ       GCATCTATTTCTGTGTCTACCCAGTGCCTGCCTGGTTTCTGATACCAATTA    1245
PCRD4.SEQ        GCATCTATTTCTGTGTCTACCCAGTGCCTGCCTGGTTTCTGATACCAATTA    1298

XGCTCTCAATAAATATXTXTXGCTTTXAATCAAAXX
                          1310          1320          1330
NMKT7.SEQ                                                                              461
NMLRDH.SEQ       NGCTCTCAATAAATATNTNT-GCTTTNAATCAAAA    1278
PCRD4.SEQ        GGCTCTCAATAAATATATGTATTGCTTTAAATCAAAAA    1334
```

MOUSE AND HUMAN 9-CIS-RETINOL DEHYDROGENASE

The invention disclosed was herein made in the course of work under NIH Grant No. R01DK 52444 from the The National Institutes of Health. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

All-trans- and 9-cis-retinoic acid are active retinoids for regulating expression of retinoid responsive genes, serving as ligands for two classes of ligand-dependent transcription factors, the retinoic acid receptors and retinoid X receptors. Little is known, however, regarding 9-cis-retinoic acid formation. We have obtained a 1.4-kilobase cDNA clone from a normalized human breast tissue library, which when expressed in CHO cells encodes a protein that avidly catalyzes oxidation of 9-cis-retinol to 9-cis-retinaldehyde. This protein also catalyzes oxidation of 13-cis-retinol at a rate approximately 10% of that of the 9-cis isomer but does not catalyze all-trans-retinol oxidation. NAD+ was the preferred electron acceptor for oxidation of 9-cis-retinol, although NADP+ supported low rates of 9-cis-retinol oxidation. The rate of 9-cis-retinol oxidation was optimal at pHs between 7.5 and 8. Sequence analysis indicates that the cDNA encodes a protein of 319 amino acids that resembles members of the short chain alcohol dehydrogenase protein family. mRNA for the protein is most abundant in human mammary tissue followed by kidney and testis, with lower levels of expression in liver, adrenals, lung, pancreas, and skeletal muscle. We propose that this cDNA encodes a previously unknown stereospecific enzyme, 9-cis-retinol dehydrogenase, which probably plays a role in 9-cis-retinoic acid formation.

Retinoids (vitamin A and its analogs) are essential dietary substances that are needed by mammals for reproduction, normal embryogenesis, growth, vision, and maintaining normal cellular differentiation and the integrity of the immune system (1–5). Within cells, retinoids regulate gene transcription acting through ligand-dependent transcription factors, the retinoic acid receptors (RARs)[1], and the retinoid X receptors (RXRs) (6,7). All-trans-retinoic acid binds only to RARs with high affinity, whereas its 9-cis isomer binds with high affinity to both RARs and RXRs. The actions of all-trans- and 9-cis-retinoic acid in regulating cellular responses are distinct and not interchangeable.

In contrast to the great explosion of information regarding the actions of retinoid receptors in regulating gene transcription, information regrading how the abundant precursor retinol is physiologically activated to form the ligands needed to activate retinoid receptors is only slowly emerging (see Refs. 8 and 9 for recent reviews). It is clear that the pathway for conversion of retinol to retinoic acid involves first the oxidation of retinol to retinaldehyde and then the oxidation of retinaldehyde to retinoic acid. Numerous enzymes that are able to catalyze either retinol or retinaldehyde oxidation have been identified, purified, and/or characterized (8–10). These enzymes are members of four distinct families: the alcohol dehydrogenases, the short chain alcohol dehydrogenases, the aldehyde dehydrogenases, and cytochrome P-450s (8–10). At present, the most attention has focused on enzymes responsible for the oxidation of all-trans-retinol to all-trans-retinaldehyde (11–15). Several recent reports have indicated that both alcohol dehydrogenases and short chain alcohol dehydrogenases may be responsible for catalyzing all-trans-retinol oxidation (11–15), but the exact in vivo roles of each of these dehydrogenases in all-trans-retinoic acid formation remains controversial (8).

9-cis-Retinoic acid has been reported to be present in mammalian tissues and cells (16–18), but it has not been convincingly established how 9-cis-retinoic acid is formed within tissues and cells. Urbach and Rando have reported that liver microsomes can nonenzymatically catalyze the isomerization of all-trans-retinoic acid to the 9-cis isomer (19). Others have demonstrated that 9-cis-β-carotene can be converted to 9-cis-retinoic acid within rat tissues (20). However, this latter pathway cannot be an essential one for 9-cis-retinoic acid formation because rats maintained on a β-carotene-free purified diet containing only retinol as a precursor for retinoic acid formation are normal. In this communication, we report the characterization of a cDNA clone for a novel human enzyme that we have designated 9-cis-retinol dehydrogenase (9cRDH) and that catalyzes in a stereospecific manner the oxidation of 9-cis-retinol to 9-cis-retinaldehyde, a first enzymatic step needed for 9-cis-retinoic acid formation. Because it has been established that 9-cis-retinaldehyde can be further oxidized to 9-cis-retinoic acid by abundant tissue retinaldehyde dehydrogenases (21–23), it is possible that 9cRDH catalyzes a key oxidation step in the formation of 9-cis-retinoic acid.

SUMMARY OF THE INVENTION

This invention provides an isolated nucleic acid molecule encoding a mammalian 9-cis-retinol dehydrogenase. In a preferred embodiment the isolated nucleic acid is a cDNA molecule which encodes a human 9-cis-retinol dehydrogenase. In an embodiment the cDNA molecule encodes a mouse 9-cis-retinol dehydrogenase. In another preferred embodiment the isolated nucleic acid molecule has the nucleotide sequence shown in FIG. 1A (SEQ. ID NO: 1). In another embodiment the isolated nucleic acid molecule has the nucleotide sequence shown in SEQ. ID NO: 6. In yet another embodiment the isolated nucleic acid molecule has the nucleotide sequence shown in SEQ. ID NO: 7. In still another embodiment the isolated nucleic acid molecule has the nucleotide sequence shown in SEQ. ID NO: 8.

This invention provides a purified 9-cis-retinol dehydrogenase. In an embodiment a 9-cis-retinol dehydrogenase is encoded by the isolated nucleic acid molecule encoding a mammalian 9-cis-retinol dehydrogenase. In a preferred embodiment the 9-cis-retinol dehydrogenase has the amino acid sequence set forth in FIG. 1B (SEQ. ID NO: 2).

This invention provides a mouse 9-cis-retinol dehydrogenase, wherein the nucleic acid molecule encoding the 9-cis-retinol dehydrogenase has the nucleotide sequence shown in any of SEQ. ID NOS: 6, 7, and 8.

This invention also provides a vector comprising the isolated mammalian nucleic acid molecule encoding a mammalian 9-cis-retinol dehydrogenase. In an embodiment the vector is a plasmid.

In an embodiment, a full-length cDNA nucleic acid molecule encoding a human 9-cis-retinol dehydrogenase is inserted by EcoR1/Not1 into a pCDNA3 plasmid (Invitrogen®) and the resulting plasmid is designated as pCDNA3-1. In an embodiment, a full-length cDNA nucleic acid molecule encoding a mouse liver 9-cis-retinol dehydrogenase is inserted by EcoR1/Not1 into a pCDNA3 plasmid (Invitrogen®) and the resulting plasmid is designated as pCDNA3-2. In an embodiment, a full-length cDNA nucleic acid molecule encoding a mouse kidney 9-cis-retinol dehydrogenase is inserted by EcoR1/Not1 into a pCDNA3 plasmid (Invitrogen®) and the resulting plasmid is designated as pCDNA3-3. In an embodiment, a full-length cDNA nucleic acid molecule encoding a mouse testis 9-cis-retinol dehydrogenase is inserted by EcoR1/Not1 into a pCDNA3 plasmid (Invitrogen®) and the resulting plasmid is designated as pCDNA3-4.

This invention provides a nucleic acid probe comprising a nucleic acid molecule of at least 15 nucleotides capable of specifically hybridizing with a unique sequence included within the sequence of an isolated nucleic acid molecule encoding a mammalian 9-cis-retinol dehydrogenase.

This invention provides a nucleic acid probe comprising a nucleic acid molecule of at least 15 nucleotides which is complementary to a sequence of the isolated nucleic acid molecule encoding a mammalian 9-cis-retinol dehydrogenase.

This invention provides a method of detecting expression of a mammalian 9-cis-retinol dehydrogenase in a cell which comprises: a) incubating a sample of cells with a retinol and an electron acceptor under conditions permitting oxidation of retinol to retinaldehyde; b) separating the resulting retinol and the retinaldehyde; and c) determining the quantities of the retinol and the retinaldehyde separated in step (b), thereby detecting expression of a mammalian 9-cis-retinol dehydrogenase in the cell.

This invention provides a method of detecting expression of a mammalian 9-cis-retinol dehydrogenase in a tissue which comprises: a) isolating total mRNA from a sample of the tissue; b) contacting the total mRNA with a nucleic acid probe capable of specifically hybridizing with a unique sequence included within the sequence of a nucleic acid molecule encoding a mammalian 9-cis-retinol dehydrogenase, wherein the sequence of a nucleic acid molecule encoding a mammalian 9-cis-retinol dehydrogenase is labeled with a detectable marker, under hybridizing conditions; and c) detecting the presence of mRNA which has hybridized to the nucleic acid probe capable of specifically hybridizing with a unique sequence included within the sequence of a nucleic acid molecule encoding a mammalian 9-cis-retinol dehydrogenase, thereby detecting expression of a mammalian 9-cis-retinol dehydrogenase in the tissue.

This invention further provides a method of detecting an compound capable of inhibiting a 9-cis-retinol dehydrogenase which comprises: a) incubating a 9-cis-retinol dehydrogenase and an electron acceptor under conditions permitting oxidation of a retinol to a retinaldehyde; b) separating the resulting retinol and the retinaldehyde produced in step (a); c) incubating a compound capable of inhibiting a 9-cis-retinol dehydrogenase with a 9-cis-retinol dehydrogenase and an electron acceptor under conditions permitting inhibition of oxidation of a retinol to a retinaldehyde, the 9-cis-retinol dehydrogenase and the electron acceptor being the same 9-cis-retinol dehydrogenase and the same electron acceptor incubated in step (a); d) separating the resulting retinol and the retinaldehyde produced in step (c); e) determining the quantities of the retinol and the retinaldehyde separated in steps (b) and (d), respectively, a smaller quantity of retinaldehyde and a greater quantity of retinol determined in step (d) indicating an inhibition of 9-cis-retinol dehydrogenase activity; and f) comparing the amount of inhibition of 9-cis-retinol dehydrogenase activity in step (d) with the amount of retinaldehyde and retinol resulting in step (b), a 50% inhibition of oxidation of retinol to retinaldehyde in step (d) indicating that the compound is capable of inhibiting the 9-cis-retinol dehydrogenase.

This invention provides a method of detecting an compound capable of inhibiting a 9-cis-retinol dehydrogenase in vitro, comprising: a) incubating a sample of cells with retinol and an electron acceptor under conditions permitting oxidation of retinol to retinaldehyde; b) separating the resulting retinol and the retinaldehyde produced in step (a); c) incubating a sample of cells, the cells being the same type of cells as the cells incubated in step (a), with a compound capable of inhibiting a 9-cis-retinol dehydrogenase under conditions permitting inhibition of oxidation of retinol to retinaldehyde; d) separating the resulting retinol and the retinaldehyde produced in step (c); e) determining the quantities of the retinol and the retinaldehyde separated in steps (b) and (d), respectively, a smaller quantity of retinaldehyde and a greater quantity of retinol determined in step (d) indicating an inhibition of 9-cis-retinol dehydrogenase activity; and f) comparing the amount of inhibition of 9-cis-retinol dehydrogenase activity in step (d) with the amount of retinaldehyde and retinol resulting in step (b), a 50% inhibition of oxidation of retinol to retinaldehyde in step (d) indicating that the compound is capable of inhibiting the 9-cis-retinol dehydrogenase in vitro.

This invention provides a method of detecting an compound capable of inhibiting a 9-cis-retinol dehydrogenase in vivo, comprising: a) administering a suitable dose of a compound capable of inhibiting a 9-cis-retinol dehydrogenase to a mammal; b) detecting in a tissue sample from the mammal in step (a) a presence of a retinol and a retinaldehyde; c) detecting in a tissue sample from a second mammal a presence of a retinol and a retinaldehyde; d) determining the quantities of the retinol and the retinaldehyde detected in steps (b) and (c), respectively, a smaller quantity of retinaldehyde and a greater quantity of retinol determined in step (b) indicating an inhibition of 9-cis-retinol dehydrogenase activity; and e) determining the amount of inhibition of 9-cis-retinol dehydrogenase activity in step (d), a 50% inhibition of 9-cis-retinol dehydrogenase activity indicating that the compound is capable of inhibiting the 9-cis-retinol dehydrogenase in vivo.

This invention provides a method of detecting an compound capable of inhibiting a 9-cis-retinol dehydrogenase which comprises: a) incubating a 9-cis-retinol dehydrogenase and an electron donor under conditions permitting reduction of a retinaldehyde to a retinol; b) separating the resulting retinol and the retinaldehyde produced in step (a); c) incubating a compound capable of inhibiting a 9-cis-retinol dehydrogenase with a 9-cis-retinol dehydrogenase and an electron donor under conditions permitting reduction of a retinaldehyde to a retinol, the 9-cis-retinol dehydrogenase and the electron donor being the same 9-cis-retinol dehydrogenase and the same electron donor incubated in step (a); d) separating the resulting retinol and the retinaldehyde produced in step (c); e) determining the quantities of the retinol and the retinaldehyde separated in steps (b) and (d), respectively, a larger quantity of retinaldehyde and a smaller quantity of retinol determined in step (d) indicating an inhibition of 9-cis-retinol dehydrogenase activity; and f) determining the amount of inhibition of 9-cis-retinol dehydrogenase activity in step (e), a 50% inhibition of reduction of retinaldehyde to retinol indicating that the compound is capable of inhibiting the 9-cis-retinol dehydrogenase.

This invention provides a method of detecting an compound capable of inhibiting a 9-cis-retinol dehydrogenase in vitro, comprising: a) incubating a sample of cells with retinol and an electron donor under conditions permitting reduction of a retinaldehyde to a retinol; b) separating the resulting retinol and the retinaldehyde produced in step (a); c) incubating a sample of cells, the cells being the same type of cells as the cells incubated in step (a), with a compound capable of inhibiting a 9-cis-retinol dehydrogenase under conditions permitting reduction of a retinaldehyde to a retinol, the 9-cis-retinol dehydrogenase and the electron donor being the same 9-cis-retinol dehydrogenase and the same electron donor incubated in step (a); d) separating the resulting retinol and the retinaldehyde produced in step (c); e) determining the quantities of the retinol and the retinaldehyde separated in steps (b) and (d), respectively, a larger quantity of retinaldehyde and a smaller quantity of retinol determined in step (d) indicating an inhibition of 9-cis-retinol dehydrogenase activity; and f) determining the amount of inhibition of 9-cis-retinol dehydrogenase activity in step (e), a 50% inhibition of reduction of retinaldehyde to retinol indicating that the compound is capable of inhibiting the 9-cis-retinol dehydrogenase in vitro.

This invention provides a method of detecting an compound capable of inhibiting a 9-cis-retinol dehydrogenase in vivo, comprising: a) administering a suitable dose of a compound capable of inhibiting a 9-cis-retinol dehydrogenase to a mammal; b) detecting in a tissue sample from the mammal in step (a) a presence of a retinol and a retinaldehyde; c) detecting in a tissue sample from a second mammal a presence of a retinol and a retinaldehyde; d) determining the quantities of the retinol and the retinaldehyde detected in steps (b) and (c), respectively, a larger quantity of retinaldehyde and a smaller quantity of retinol determined in step (b) indicating an inhibition of 9-cis-retinol dehydrogenase activity; e) determining the amount of inhibition of 9-cis-retinol dehydrogenase activity in step (d), a 50% inhibition of 9-cis-retinol dehydrogenase activity indicating that the compound is capable of inhibiting the 9-cis-retinol dehydrogenase in vivo.

This invention also provides a method of determining a toxic compound capable of inhibiting a 9-cis-retinol dehydrogenase comprising the method of any of the above-described methods of detecting an compound capable of inhibiting a 9-cis-retinol dehydrogenase, wherein an ability of a small concentration of the compound to inhibiting 50% of the 9-cis-retinol dehydrogenase activity indicates that the compound is toxic.

This invention provides a method for detecting a predisposition to cancer associated with the expression of a 9-cis-retinol dehydrogenase in a sample from a subject which comprises: a) determining the amount of expression of a 9-cis-retinol dehydrogenase in a cancerous tissue by performing the method of either of claims 40 and 43 on a sample of cells from the cancerous tissue; b) determining the amount of expression of a 9-cis-retinol dehydrogenase in a sample from a subject; and c) comparing the level of expression of 9-cis-retinol dehydrogenase in the sample from the subject with the level of expression of 9-cis-retinol dehydrogenase in the sample from the cancerous tissue, a comparable level of expression of 9-cis-retinol dehydrogenase indicating a predisposition to cancer in the subject.

This invention provides a method for detecting a predisposition to a cancer or to a disease associated with the either an overexpression or an underexpression of a human 9-cis-retinol dehydrogenase in a sample from a subject which comprises: a) obtaining DNA from the sample of the subject suffering from cancer or from the disease associated with either an overexpression or an underexpression of a human 9-cis-retinol dehydrogenase; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; e) detecting labeled DNA fragments which have hybridized to the nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase creates a unique band pattern specific to the DNA of subjects suffering from cancer; f) preparing DNA obtained from a sample of a subject for diagnosis by steps (a–e); and g) comparing the detected band pattern specific to the DNA obtained from a sample of subjects suffering from cancer or from the disease associated with either an overexpression or an underexpression of a human 9-cis-retinol dehydrogenase from step (e) and the DNA obtained from a sample of the subject for diagnosis from step (f) to determine whether the patterns are the same or different and to diagnose thereby predisposition to the cancer or the disease associated with the overexpression or the underexpression of the human 9-cis-retinol dehydrogenase if the patterns are the same.

This invention provides a method for detecting a predisposition to a cancer or to a disease associated with an overexpression of a human 9-cis-retinol dehydrogenase in a sample from a subject which comprises: a) obtaining DNA from the sample of the subject suffering from cancer or from the disease associated with an overexpression of a human 9-cis-retinol dehydrogenase; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; e) detecting labeled DNA fragments which have hybridized to the nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase creates a unique band pattern specific to the DNA of subjects suffering from cancer; f) preparing DNA obtained from a sample of a subject for diagnosis by steps (a–e); and g) comparing the detected band pattern specific to the DNA obtained from a sample of subjects suffering from the cancer or from the disease associated with the overexpression of a human 9-cis-retinol dehydrogenase from step (e) and the DNA obtained from a sample of the subject for diagnosis from step (f) to determine whether the patterns are the same or different and to diagnose thereby predisposition to the cancer or the disease associated with the overexpression of the human 9-cis-retinol dehydrogenase if the patterns are the same.

This invention provides a method for detecting a predisposition to a cancer or to a disease associated with an underexpression of a human 9-cis-retinol dehydrogenase in a sample from a subject which comprises: a) obtaining DNA from the sample of the subject suffering from cancer or from the disease associated with an underexpression of a human 9-cis-retinol dehydrogenase; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; e) detecting labeled DNA fragments which have hybridized to the nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase creates a unique band pattern specific to the DNA of subjects suffering from cancer; f) preparing DNA obtained from a sample of a subject for diagnosis by steps (a–e); and g) comparing the detected band pattern specific to the DNA obtained from a sample of subjects suffering from cancer or from the disease associated with the underexpression of a human 9-cis-retinol dehydrogenase from step (e) and the DNA obtained from a sample of the subject for diagnosis from step (f) to determine whether the patterns are the same or different and to diagnose thereby predisposition to the cancer or the disease associated with the underexpression of the human 9-cis-retinol dehydrogenase if the patterns are the same.

This invention provides a method for detecting a predisposition to a cancer or a disease associated with the overexpression or under expression of a human 9-cis-retinol dehydrogenase in a sample from a subject which comprises: a) obtaining RNA from the sample of the subject suffering from the cancer or the disease associated with the overexpression or under expression of the human 9-cis-retinol dehydrogenase; b) separating the RNA sample by size fractionation; c) contacting the resulting RNA species with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; d) detecting labeled bands which have hybridized to the RNA species to create a unique band pattern specific to the RNA of subjects suffering from the cancer or the disease associated with the overexpression or under expression of the human 9-cis-retinol dehydrogenase; e) preparing RNA obtained from a sample of a subject for diagnosis by steps (a–d); and f) comparing the detected band pattern specific to the RNA obtained from a sample of subjects suffering from the cancer or the disease associated with the overexpression or under expression of a human 9-cis-retinol dehydrogenase from step (d) and the RNA obtained from a sample of the subject for diagnosis from step (f) to determine whether the patterns are the same or different and to diagnose thereby predisposition to the cancer or the disease associated with the overexpression or underexpression of the human 9-cis-retinol dehydrogenase if the patterns are the same.

This invention provides an antisense oligonucleotide having a sequence capable of specifically hybridizing to an mRNA molecule encoding a human 9-cis-retinol dehydrogenase so as to prevent expression of the mRNA molecule.

In an embodiment the antisense oligonucleotide has a sequence capable of specifically hybridizing to the isolated cDNA molecule encoding a mammalian 9-cis-retinol dehydrogenase.

This invention provides a purified 9-cis-retinol dehydrogenase, wherein the 9-cis-retinol dehydrogenase is a human 9-cis-retinol dehydrogenase.

This invention provides an antibody directed to a purified 9-cis-retinol dehydrogenase or to a purified 9-cis-retinol dehydrogenase, wherein the 9-cis-retinol dehydrogenase is a human 9-cis-retinol dehydrogenase.

This invention provides an antibody capable of specifically recognizing 9-cis-retinol dehydrogenase. In an embodiment the antibody may be a polyclonal antibody. In another embodiment the antibody may be a monoclonal antibody.

This invention provides an antibody capable of specifically recognizing unique amino acid residues of 9-cis-retinol dehydrogenase. In a preferred embodiment of the antibody the unique amino acid residues of 9-cis-retinol dehydrogenase are HYGGAFLKYLKMQQRIMNLI (SEQ ID NO: 9).

This invention provides a method of detecting expression of a mammalian 9-cis-retinol dehydrogenase in a tissue or cells from a sample which comprises: a) incubating a sample of the tissue or cells from a sample with an antibody which specifically recognizes 9-cis-retinol dehydrogenase and is labeled with a detectable marker under conditions permitting a binding of the antibody to the tissue or the cells; and b) detecting labeled tissue or cells, thereby detecting expression of the mammalian 9-cis-retinol dehydrogenase in the tissue or the cells.

This invention provides a method of detecting human 9-cis-retinol dehydrogenase in a sample which comprises: a) contacting the sample with of any of the above-described antibodies under conditions permitting the formation of a complex between the antibody and the human 9-cis-retinol dehydrogenase in the sample; and b) detecting the complex formed in step (a) thereby detecting the presence of human 9-cis-retinol dehydrogenase in the sample.

This invention provides a method of detecting a disease which is responsive to treatment with a retinoid, comprising the method of detecting human 9-cis-retinol dehydrogenase in a tissue or cells from a sample, wherein the detection of the expression of the mammalian 9-cis-retinol dehydrogenase indicates the disease is responsive to retinoic acid treatment.

This invention provides a method of detecting a disease which is refractory to treatment with a retinoid comprising the method of detecting human 9-cis-retinol dehydrogenase in a tissue or cells from a sample, wherein the detection of the expression of the mammalian 9-cis-retinol dehydrogenase indicates the disease is refractory to retinoic acid treatment.

This invention provides a pharmaceutical composition comprising an amount of any of the above-described oligonucleotides and effective to prevent overexpression of a human 9-cis-retinol dehydrogenase and a pharmaceutically acceptable carrier capable of passing through a cell membrane.

This invention provides a recombinant non-human vertebrate animal wherein the functional 9-cis-retinol dehydrogenase is not expressed.

This invention provides a recombinant non-human vertebrate animal wherein the functional 9-cis-retinol dehydrogenase is underexpressed.

This invention provides a method of treating any of the above-described recombinant non-human vertebrate animals comprising administration of a vector comprising an isolated mammalian nucleic acid molecule encoding a 9-cis-retinol dehydrogenase.

BRIEF DESCRIPTION OF THE FIGURES

FIGS. 1A–1B. FIG. 1A (SEQ. ID NO: 1), the nucleotide sequence for the cDNA clone encoding 9cRDH. The start and termination codons for the cDNA sequence of 9cRDH are underlined. FIG. 1B, the deduced amino acid sequence for the protein encoded by the cDNA clone obtained from a normalized human breast tissue library (9c) (SEQ. ID NO: 2) and, for comparison, the amino acid sequences for bovine 11cis-retinol dehydrogenase (11) (27) (SEQ. ID NO: 5), rat liver retinol dehydrogenase, type I (L1) (11) (SEQ. ID NO: 3), and rat liver retinol dehydrogenase, type II (L2) (13) (SEQ. ID NO: 4). Amino acids that are identical in each of the four protein sequences are underlined.

In FIG. 2D, 10 µM 9-cis-retinol was incubated with 38 µg of CHO cell homogenate protein obtained from cells transfected with vector alone and 2 mM NAD+. The elution positions of 13-cis-retinaldehyde (1), 9-cis-retinaldehyde (2), all-trans-retinaldehyde (3), 13-cis-retinol (4), 9-cis-retinol (5), and alltrans-retinol (6) are indicated with arrows.

FIGS. 4A–4G. Sequence analysis of full-length cDNA clones for mouse 9-cis retinol dehydrogenase obtained from kidney (NMKT7.SEQ), [SEQ ID NO: 11] liver (NMLRDH.SEQ) [SEQ ID NO: 12], and testis (PCRD4.SEQ) [SEQ ID NO: 13] cDNA libraries. Alignment [SEQ ID NO: 10] using cluster method with weighted residue weight table. X is a space, i.e. no nucleotide.

DETAILED DESCRIPTION OF THE INVENTION

Figure 2A:
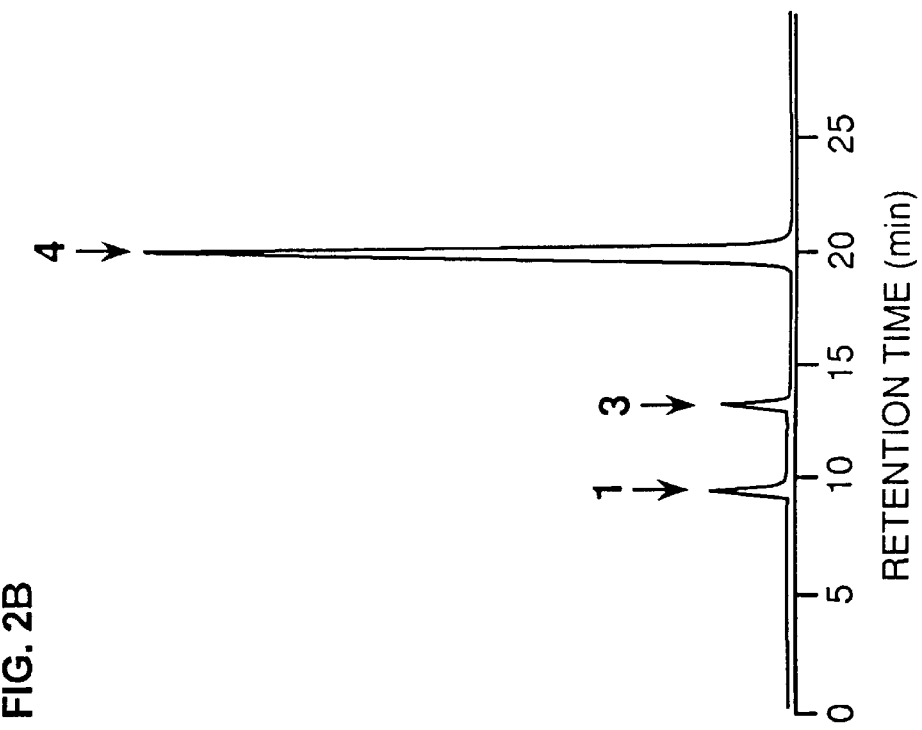
FIGS. 2A–2D. Representative HPLC profiles for extracts of incubation mixtures consisting of 10 µM 9-cis-retinol (FIG. 2A), 10 µM 13-cis-retinol (FIG. 2B), or 10 µM all-trans-retinol (FIG. 2C) and 32 µg of CHO cell homogenate protein obtained from cells transfected with vector (pcDNA3, Invitrogen) containing the cDNA insert and 2 mM NAD+.
Figure 2B:
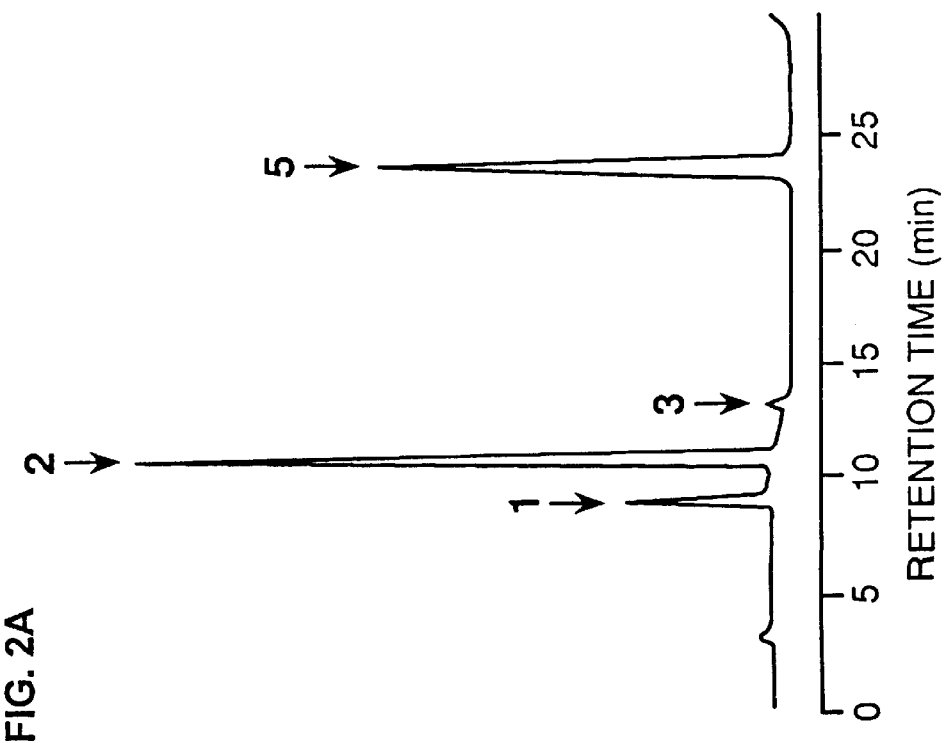
Figure 2D:
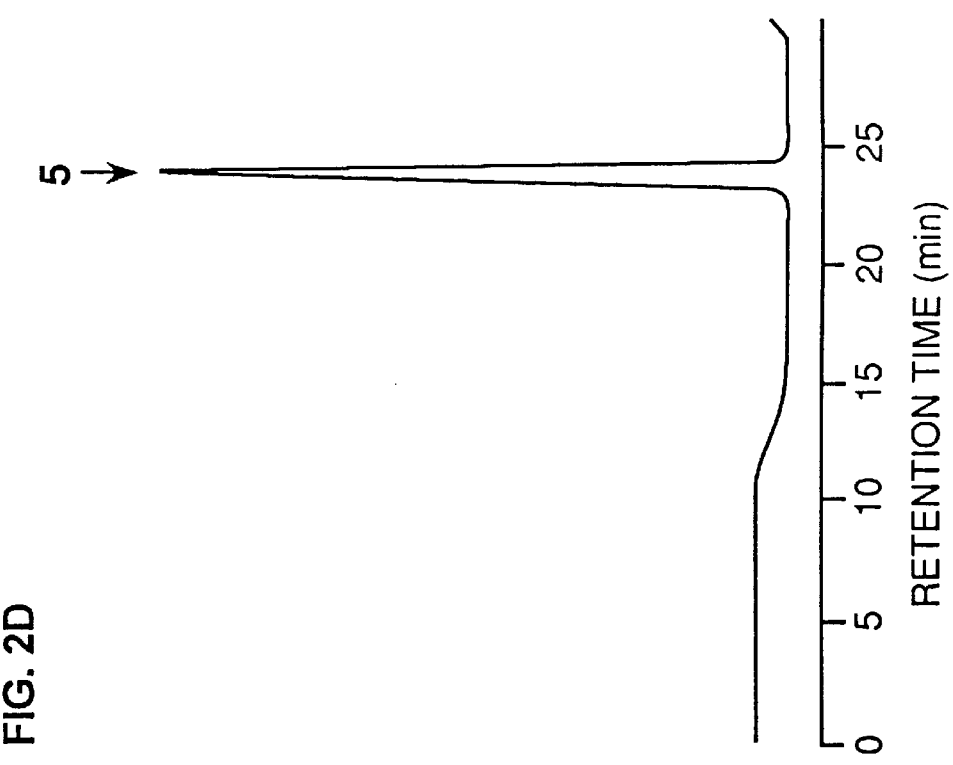
Figure 2C:
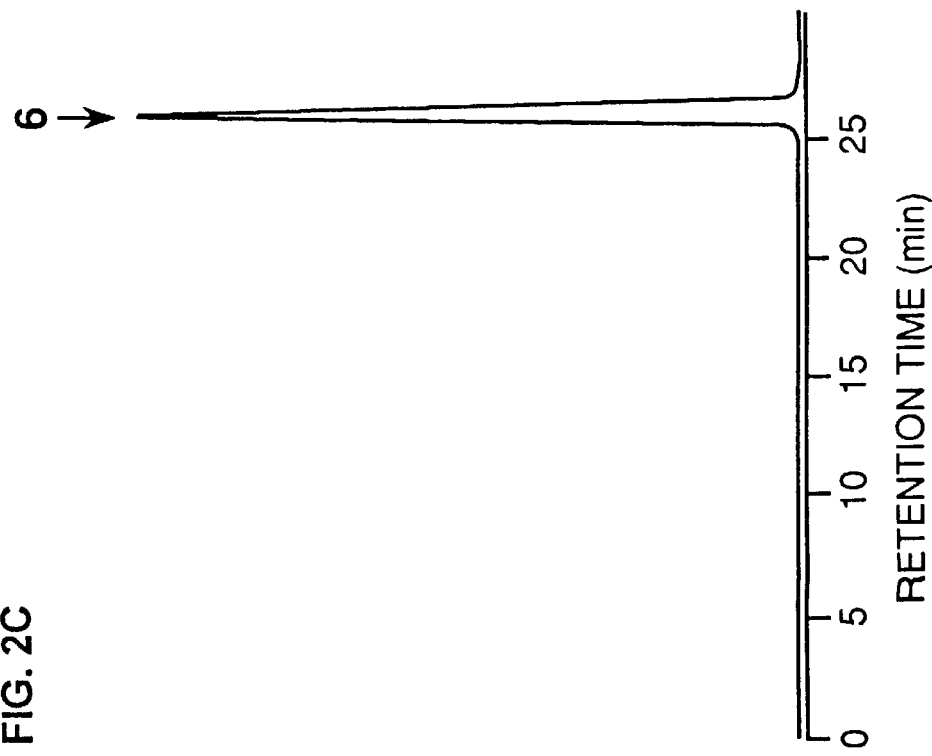

The following standard abbreviations are used throughout the specification to indicate specific nucleotides:

C=cytosine
A=adenosine
T=thymidine
G=guanosine

This invention provides an isolated nucleic acid molecule encoding a mammalian 9-cis-retinol dehydrogenase. In an embodiment the isolated nucleic acid molecule is a DNA molecule. In another embodiment the isolated DNA molecule is a full-length DNA molecule. In an embodiment the isolated DNA molecule is a cDNA molecule. In a preferred embodiment the cDNA molecule encodes a human 9-cis-retinol dehydrogenase. In an embodiment the cDNA molecule encodes a mouse 9-cis-retinol dehydrogenase. In another preferred embodiment the isolated nucleic acid molecule has the nucleotide sequence shown in FIG. 1A (SEQ. ID NO: 1). In another embodiment the isolated nucleic acid molecule has the nucleotide sequence shown in SEQ. ID NO: 6. In yet another embodiment the isolated nucleic acid molecule has the nucleotide sequence shown in SEQ. ID NO: 7. In still another embodiment the isolated nucleic acid molecule has the nucleotide sequence shown in SEQ. ID NO: 8. In a preferred embodiment of the isolated nucleic acid molecule, the encoded 9-cis-retinol dehydrogenase catalyzes oxidation of 9-cis-retinol. In another preferred embodiment of the isolated nucleic acid molecule, the encoded 9-cis-retinol dehydrogenase catalyzes oxidation of 13-cis-retinol. In still another embodiment the isolated DNA molecule is genomic DNA molecule. In another embodiment the isolated nucleic acid molecule is an RNA molecule.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide, 9-cis-retinol dehydrogenase, and as products for the large scale synthesis of the polypeptide (9-cis-retinol dehydrogenase) by a variety of recombinant techniques. The molecule is useful for generating new cloning and expression vectors, transformed and transfected prokaryotic and eukaryotic host cells, and new and useful methods for cultured growth of such host cells capable of expression of the polypeptide (9-cis-retinol dehydrogenase) and related products.

This invention provides a purified 9-cis-retinol dehydrogenase. In an embodiment a 9-cis-retinol dehydrogenase is encoded by the isolated nucleic acid molecule encoding a mammalian 9-cis-retinol dehydrogenase. In a preferred embodiment the 9-cis-retinol dehydrogenase has substantially the same amino acid sequence as shown in FIG. 1B (SEQ. ID NO: 2). In another preferred embodiment the 9-cis-retinol dehydrogenase of claim 16, wherein the 9-cis-retinol dehydrogenase has the amino acid sequence as shown in FIG. 1B (SEQ. ID NO: 2). In yet another preferred embodiment of the 9-cis-retinol dehydrogenase which may be a purified 9-cis-retinol dehydrogenase, a purified 9-cis-retinol dehydrogenase encoded by the isolated nucleic acid molecule encoding a mammalian 9-cis-retinol dehydrogenase, said purified 9-cis-retinol dehydrogenase having substantially the same amino acid sequence as shown in FIG. 1B (SEQ. ID NO: 2) or said purified 9-cis-retinol dehydrogenase having the amino acid sequence as shown in FIG. 1B (SEQ. ID NO: 2), the 9-cis-retinol dehydrogenase is a human 9-cis-retinol dehydrogenase. In another embodiment of the 9-cis-retinol dehydrogenase which may be a purified 9-cis-retinol dehydrogenase or a purified 9-cis-retinol dehydrogenase encoded by the isolated nucleic acid molecule encoding a mammalian 9-cis-retinol dehydrogenase, the 9-cis-retinol dehydrogenase is a mouse 9-cis-retinol dehydrogenase.

This invention provides a mouse 9-cis-retinol dehydrogenase, wherein the nucleic acid molecule encoding the 9-cis-retinol dehydrogenase has the nucleotide sequence shown in any of SEQ. ID NOS: 6, 7, and 8.

This invention provides an isolated nucleic acid molecule of claim 1 operatively linked to a promoter of RNA transcription.

This invention also provides a vector comprising the isolated mammalian nucleic acid molecule encoding a mammalian 9-cis-retinol dehydrogenase. In an embodiment the vector is a plasmid.

In an embodiment, a full-length cDNA nucleic acid molecule encoding a human 9-cis-retinol dehydrogenase is inserted by EcoR1/Not1 into a pCDNA3 plasmid (Invitrogen®) and the resulting plasmid is designated as pCDNA3-1. Plasmid pCDNA3-1 was deposited on Sep. 19, 1997 with the American Type Culture Collection (ATCC), 12301 Parklawn Drive, Rockville, Md. 20852, U.S.A. which is now located at 1801 University Boulevard, Manassas, Va. 20110-2209, under the provisions of the Budapest Treaty for the International Recognition of the Deposit of Microorganisms for the Purposes of Patent Procedure. Plasmid pCDNA3-1 was accorded ATCC Accession Number 209285.

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk$^-$ cells and COS cells. Mammalian cells may be transfected by methods well known in the art such as calcium phosphate precipitation, electroporation and microinjection.

One of ordinary skill in the art will easily obtain unique sequences from the cDNA cloned in the pCDNA3-1 plasmid. Such unique sequences may be used as probes to screen various mammalian cDNA libraries and genomic DNAs, e.g. mouse, rat and bovine, to obtain homologous nucleic acid sequences and to screen different cDNA tissue libraries to obtain isoforms of the obtained nucleic acid sequences. Nucleic acid probes from the cDNA cloned in the pCDNA3-1 plasmid may further be used to screen other human tissue cDNA libraries to obtain isoforms of the nucleic acid sequences encoding 9-cis-retinol dehydrogenase as well as to screen human genomic DNA to obtain the analogous nucleic acid sequences. The homologous nucleic acid sequences and isoforms may be used to produce the proteins encoded thereby.

In an embodiment, a full-length cDNA nucleic acid molecule encoding a mouse liver 9-cis-retinol dehydrogenase is inserted by EcoR1/Not1 into a pCDNA3 plasmid (Invitrogen®) and the resulting plasmid is designated as pCDNA3-2.

In an embodiment, a full-length cDNA nucleic acid molecule encoding a mouse kidney 9-cis-retinol dehydrogenase is inserted by EcoR1/Not1 into a pCDNA3 plasmid (Invitrogen®) and the resulting plasmid is designated as pCDNA3-3.

In an embodiment, a full-length cDNA nucleic acid molecule encoding a mouse testis 9-cis-retinol dehydrogenase is inserted by EcoR1/Not1 into a pCDNA3 plasmid (Invitrogen®) and the resulting plasmid is designated as pCDNA3-4. In further embodiments the vector comprising any of the plasmids designated as pCDNA3-1, pCDNA3-2, pCDNA3-3, or pCDNA3-4 may be introduced into a suitable host cell. In still further embodiments the host cell is selected from a group consisting of a bacterial cell, a plant cell, and insect cell and a mammalian cell.

This invention provides a method of producing a polypeptide having the biological activity of a mammalian 9-cis-retinol dehydrogenase which comprises growing any of the above described host cells of a vector containing the nucleic acid molecule encoding a mammalian 9-cis-retinol dehydrogenase under suitable conditions permitting production of the polypeptide and recovering the polypeptide so produced.

As used herein, the biological activity of a 9-cis-retinol dehydrogenase is defined as the ability to catalyze oxidation of retinol to retinaldehyde, as well as the ability to catalyze the reverse reaction, i.e. reduction of retinaldehyde to retinol. Accordingly, a 9-cis-retinol dehydrogenase may also be defined as a "retinaldehyde reductase", i.e. a 9-cis-retinaldehyde reductase.

This invention provides a nucleic acid probe comprising a nucleic acid molecule of at least 15 nucleotides capable of specifically hybridizing with a unique sequence included within the sequence of an isolated nucleic acid molecule encoding a mammalian 9-cis-retinol dehydrogenase. In an embodiment of the nucleic acid probe the nucleic acid molecule is DNA. In another embodiment of the nucleic acid probe the nucleic acid molecule is RNA.

This invention provides a nucleic acid probe comprising a nucleic acid molecule of at least 15 nucleotides which is complementary to a sequence of the isolated nucleic acid molecule encoding a mammalian 9-cis-retinol dehydrogenase.

In an embodiment of the nucleic acid probe the nucleic acid molecule is DNA. In another embodiment of the nucleic acid probe the nucleic acid molecule is RNA. In further embodiment any of the above described nucleic acid probes may be labeled with a detectable marker. In an embodiment of these nucleic acid probes the detectable marker may be selected from the group consisting of a radioactive isotope, enzyme, dye, biotin, a fluorescent label or a chemiluminescent label.

This invention provides a method of detecting expression of a mammalian 9-cis-retinol dehydrogenase in a cell which comprises: a) incubating a sample of cells with a retinol and an electron acceptor under conditions permitting oxidation of retinol to retinaldehyde; b) separating the resulting retinol and the retinaldehyde; and c) determining the quantities of the retinol and the retinaldehyde separated in step (b), thereby detecting expression of a mammalian 9-cis-retinol dehydrogenase in the cell. In an embodiment of this method, the retinol in step (a) is selected from the group consisting of 9-cis-retinol, 11-cis-retinol, and 13-cis-retinol. In a further embodiment of this method, the electron acceptor in step (a) is selected from the either $NAD^+$ or $NADP^+$.

This invention provides a method of detecting expression of a mammalian 9-cis-retinol dehydrogenase in a tissue which comprises: a) isolating total mRNA from a sample of the tissue; b) contacting the total mRNA with a nucleic acid probe capable of specifically hybridizing with a unique sequence included within the sequence of a nucleic acid molecule encoding a mammalian 9-cis-retinol dehydrogenase, wherein the sequence of a nucleic acid molecule encoding a mammalian 9-cis-retinol dehydrogenase is labeled with a detectable marker, under hybridizing conditions; and c) detecting the presence of mRNA which has hybridized to the nucleic acid probe capable of specifically hybridizing with a unique sequence included within the sequence of a nucleic acid molecule encoding a mammalian 9-cis-retinol dehydrogenase, thereby detecting expression of a mammalian 9-cis-retinol dehydrogenase in the tissue.

This invention further provides a method of detecting an compound capable of inhibiting a 9-cis-retinol dehydrogenase which comprises: a) incubating a 9-cis-retinol dehydrogenase and an electron acceptor under conditions permitting oxidation of a retinol to a retinaldehyde; b) separating the resulting retinol and the retinaldehyde produced in step (a); c) incubating a compound capable of inhibiting a 9-cis-retinol dehydrogenase with a 9-cis-retinol dehydrogenase and an electron acceptor under conditions permitting inhibition of oxidation of a retinol to a retinaldehyde, the 9-cis-retinol dehydrogenase and the electron acceptor being the same 9-cis-retinol dehydrogenase and the same electron acceptor incubated in step (a); d) separating the resulting retinol and the retinaldehyde produced in step (c); e) determining the quantities of the retinol and the retinaldehyde separated in steps (b) and (d), respectively, a smaller quantity of retinaldehyde and a greater quantity of retinol determined in step (d) indicating an inhibition of 9-cis-retinol dehydrogenase activity; f) comparing the amount of inhibition of 9-cis-retinol dehydrogenase activity in step (d) with the amount of retinaldehyde and retinol resulting in step (b), a 50% inhibition of oxidation of retinol to retinaldehyde in step (d) indicating that the compound is capable of inhibiting the 9-cis-retinol dehydrogenase.

In a preferred embodiment of this method, the compound capable of inhibiting a 9-cis-retinol dehydrogenase is selected from the group consisting of naturally occurring and synthetic retinoids and lipids. In another preferred embodiment the retinoids are selected from the group consisting of naturally occurring and synthetic retinoic acids and synthetic retinoic acid analogs. The retinoids include but are not limited to 13-cis retinoic acid, 9-cis retinoic acid, and lipids with chemical structures similar to 13-cis retinoic acid, e.g. oleic acid. One of skill in the art would know how to select compounds with structures similar to these or other retinoids for use in an assay(s) to determine the above described inhibition.

This invention provides a method of detecting an compound capable of inhibiting a 9-cis-retinol dehydrogenase in vitro, comprising: a) incubating a sample of cells with retinol and an electron acceptor under conditions permitting oxidation of retinol to retinaldehyde; b) separating the resulting retinol and the retinaldehyde produced in step (a); c) incubating a sample of cells, the cells being the same type of cells as the cells incubated in step (a), with a compound capable of inhibiting a 9-cis-retinol dehydrogenase under conditions permitting inhibition of oxidation of retinol to retinaldehyde; d) separating the resulting retinol and the retinaldehyde produced in step (c); e) determining the quantities of the retinol and the retinaldehyde separated in steps (b) and (d), respectively, a smaller quantity of retinaldehyde and a greater quantity of retinol determined in step (d) indicating an inhibition of 9-cis-retinol dehydrogenase activity; f) comparing the amount of inhibition of 9-cis-retinol dehydrogenase activity in step (d) with the amount of retinaldehyde and retinol resulting in step (b), a 50% inhibition of oxidation of retinol to retinaldehyde in step (d) indicating that the compound is capable of inhibiting the 9-cis-retinol dehydrogenase in vitro.

In a preferred embodiment of this method, the compound capable of inhibiting a 9-cis-retinol dehydrogenase is selected from the group consisting of naturally occurring and synthetic retinoids and lipids. In another preferred embodiment the retinoids are selected from the group consisting of naturally occurring and synthetic retinoic acids and synthetic retinoic acid analogs. The retinoids include but are not limited to 13-cis retinoic acid, 9-cis retinoic acid, and lipids with chemical structures similar to 13-cis retinoic acid, e.g. oleic acid. One of skill in the art would know how to select compounds with structures similar to these or other retinoids for use in an assay(s) to determine the above described inhibition.

This invention provides a method of detecting an compound capable of inhibiting a 9-cis-retinol dehydrogenase in vivo, comprising: a) administering a suitable dose of a compound capable of inhibiting a 9-cis-retinol dehydrogenase to a mammal; b) detecting in a tissue sample from the mammal in step (a) a presence of a retinal and a retinaldehyde; c) detecting in a tissue sample from a second mammal a presence of a retinal and a retinaldehyde; d) determining the quantities of the retinal and the retinaldehyde detected in steps (b) and (c), respectively, a smaller quantity of retinaldehyde and a greater quantity of retinal determined in step (b) indicating an inhibition of 9-cis-retinol dehydrogenase activity; e) determining the amount of inhibition of 9-cis-retinol dehydrogenase activity in step (d), a 50% inhibition of 9-cis-retinol dehydrogenase activity indicating that the compound is capable of inhibiting the 9-cis-retinol dehydrogenase in vivo.

In a preferred embodiment of this method, the compound capable of inhibiting a 9-cis-retinol dehydrogenase is selected from the group consisting of naturally occurring and synthetic retinoids and lipids. In another preferred embodiment the retinoids are selected from the group consisting of naturally occurring and synthetic retinoic acids and synthetic retinoic acid analogs. The retinoids include but are not limited to 13-cis retinoic acid, 9-cis retinoic acid, and lipids with chemical structures similar to 13-cis retinoic acid, e.g. oleic acid. One of skill in the art would know how to select compounds with structures similar to these or other retinoids for use in an assay(s) to determine the above described inhibition.

This invention provides a method of detecting an compound capable of inhibiting a 9-cis-retinol dehydrogenase which comprises: a) incubating a 9-cis-retinol dehydrogenase and an electron donor under conditions permitting reduction of a retinaldehyde to a retinol; b) separating the resulting retinol and the retinaldehyde produced in step (a); c) incubating a compound capable of inhibiting a 9-cis-retinol dehydrogenase with a 9-cis-retinol dehydrogenase and an electron donor under conditions permitting reduction of a retinaldehyde to a retinol, the 9-cis-retinol dehydrogenase and the electron donor being the same 9-cis-retinol dehydrogenase and the same electron donor incubated in step (a); d) separating the resulting retinol and the retinaldehyde produced in step (c); e) determining the quantities of the retinol and the retinaldehyde separated in steps (b) and (d), respectively, a larger quantity of retinaldehyde and a smaller quantity of retinol determined in step (d) indicating an inhibition of 9-cis-retinol dehydrogenase activity; f) determining the amount of inhibition of 9-cis-retinol dehydrogenase activity in step (e), a 50% inhibition of reduction of retinaldehyde to retinol indicating that the compound is capable of inhibiting the 9-cis-retinol dehydrogenase. In a preferred embodiment of this method, the compound capable of inhibiting a 9-cis-retinol dehydrogenase is selected from the group consisting of naturally occurring and synthetic retinoids and lipids. In another preferred embodiment the retinoids are selected from the group consisting of naturally occurring and synthetic retinoic acids and synthetic retinoic acid analogs. The retinoids include but are not limited to 13-cis retinoic acid, 9-cis retinoic acid, and lipids with chemical structures similar to 13-cis retinoic acid, e.g. oleic acid. One of skill in the art would know how to select compounds with structures similar to these or other retinoids for use in an assay(s) to determine the above described inhibition.

This invention provides a method of detecting an compound capable of inhibiting a 9-cis-retinol dehydrogenase in vitro, comprising: a) incubating a sample of cells with retinol and an electron donor under conditions permitting reduction of a retinaldehyde to a retinol; b) separating the resulting retinol and the retinaldehyde produced in step (a); c) incubating a sample of cells, the cells being the same type of cells as the cells incubated in step (a), with a compound capable of inhibiting a 9-cis-retinol dehydrogenase under conditions permitting reduction of a retinaldehyde to a retinol, the 9-cis-retinol dehydrogenase and the electron donor being the same 9-cis-retinol dehydrogenase and the same electron donor incubated in step (a); d) separating the resulting retinol and the retinaldehyde produced in step (c); e) determining the quantities of the retinol and the retinaldehyde separated in steps (b) and (d), respectively, a larger quantity of retinaldehyde and a smaller quantity of retinol determined in step (d) indicating an inhibition of 9-cis-retinol dehydrogenase activity; f) determining the amount of inhibition of 9-cis-retinol dehydrogenase activity in step (e), a 50% inhibition of reduction of retinaldehyde to retinal indicating that the compound is capable of inhibiting the 9-cis-retinol dehydrogenase in vitro.

In a preferred embodiment of this method, the compound capable of inhibiting a 9-cis-retinol dehydrogenase is selected from the group consisting of naturally occurring and synthetic retinoids and lipids. In another preferred embodiment the retinoids are selected from the group consisting of naturally occurring and synthetic retinoic acids and synthetic retinoic acid analogs. The retinoids include but are not limited to 13-cis retinoic acid, 9-cis retinoic acid, and lipids with chemical structures similar to 13-cis retinoic acid, e.g. oleic acid. One of skill in the art would know how to select compounds with structures similar to these or other retinoids for use in an assay(s) to determine the above described inhibition.

This invention provides a method of detecting an compound capable of inhibiting a 9-cis-retinol dehydrogenase in vivo, comprising: a) administering a suitable dose of a compound capable of inhibiting a 9-cis-retinol dehydrogenase to a mammal; b) detecting in a tissue sample from the mammal in step (a) a presence of a retinal and a retinaldehyde; c) detecting in a tissue sample from a second mammal a presence of a retinal and a retinaldehyde; d) determining the quantities of the retinal and the retinaldehyde detected in steps (b) and (c), respectively, a larger quantity of retinaldehyde and a smaller quantity of retinol determined in step (b) indicating an inhibition of 9-cis-retinol dehydrogenase activity; e) determining the amount of inhibition of 9-cis-retinol dehydrogenase activity in step (d), a 50% inhibition of 9-cis-retinol dehydrogenase activity indicating that the compound is capable of inhibiting the 9-cis-retinol dehydrogenase in vivo.

In a preferred embodiment of this method, the compound capable of inhibiting a 9-cis-retinol dehydrogenase is selected from the group consisting of naturally occurring and synthetic retinoids and lipids. In another preferred embodiment the retinoids are selected from the group consisting of naturally occurring and synthetic retinoic acids and synthetic retinoic acid analogs. The retinoids include but are not limited to 13-cis retinoic acid, 9-cis retinoic acid, and lipids with chemical structures similar to 13-cis retinoic acid, e.g. oleic acid. One of skill in the art would know how to select compounds with structures similar to these or other retinoids for use in an assay(s) to determine the above described inhibition.

This invention also provides a method of determining a toxic compound capable of inhibiting a 9-cis-retinol dehydrogenase comprising the method of any of the above-described methods of detecting an compound capable of inhibiting a 9-cis-retinol dehydrogenase, wherein an ability of a small concentration of the compound to inhibiting 50% of the 9-cis-retinol dehydrogenase activity indicates that the compound is toxic.

The above-described methods may be used to develop, e.g. synthesize new or improved drugs, e.g. less toxic retinoids, or more specific drugs, e.g. retinoids binding to or interacting with particular retinoid receptors, e.g. such as all-trans retinoic acid which binds to or interacts with retinoic acid receptors (RARs), or 9-cis retinoic acid which binds to or interacts with retinoid X receptors (RXRs). RARs regulate retinoid responsive genes. RXRs regulate retinoid, thyroid hormone, vitamin D, proxisomal proliferator and other responsive genes. Accordingly, above-described screening methods may be used to develop new or improved drugs relating to any regulatory aspects of retinoids, e.g. the gene expression or at the receptor(s) ligand binding site(s) for enhancing interaction or stimulating interaction between ligands and receptors.

The above-described methods may be used to develop synthetic inhibitors (or regulators) of the 9-cis-retinol dehydrogenase or 13-cis-retinol dehydrogenase based on the interaction of the 9-cis-retinol dehydrogenase or 13-cis-retinol dehydrogenase and their respective substrates and the determination of their lower toxicity (as compared to the highly toxic compounds screened supra) so as to produce drugs which are therapeutic. Moreover, new drugs may be developed which regulate the pathway of the 9-cis-retinol dehydrogenase or 13-cis-retinol dehydrogenase, e.g. biological activities catalyzed thereby.

The new or improved drugs, include but are not limited to retinoids, and may be used to treat a variety of diseases, including but not limited to dermatologic conditions such as acne or psoriasis, diabetes or lipid disorders indiabetes, for blocking collagenase production in arthritis, for pulmonary diseases such as asthma, and for chemoprevention induction (lessening the toxicity of chemotherapy) and continuation of remission in the treatment of cancer. One of skill in the art will appreciate the many applications of new or improved drugs such as retinoids.

The above-described methods may be used to determine the toxicity of compounds other than retinoids. In an embodiment the compounds may be steroids. Accordingly, any of the above-described methods for detecting a compound capable of inhibiting a 9-cis-retinol dehydrogenase in vitro or in vivo may be used to detect an inhibition of a 9-cis-retinol dehydrogenase by a steroid. In another embodiment, of any the above-described methods, an ability of a small concentration of a steroid to inhibit 50% of the 9-cis-retinol dehydrogenase activity indicates that the steroid is toxic.

In an embodiment of the above-described for determining a toxic compound, the method may be used for screening for a potential therapeutic compound, wherein the 50% inhibition of a 9-cis-retinol dehydrogenase by a small concentration of several compounds is compared to determine the respective toxicities of the compounds, a determination of a higher toxicity by a smaller concentration of a compound indicating that the compound is not a potential therapeutic compound.

This invention provides a method for detecting a predisposition to cancer associated with the expression of a 9-cis-retinol dehydrogenase in a sample from a subject which comprises: a) determining the amount of expression of a 9-cis-retinol dehydrogenase in a cancerous tissue by performing the method of either of claims 40 and 43 on a sample of cells from the cancerous tissue; b) determining the amount of expression of a 9-cis-retinol dehydrogenase in a sample from a subject; and c) comparing the level of expression of 9-cis-retinol dehydrogenase in the sample from the subject with the level of expression of 9-cis-retinol dehydrogenase in the sample from the cancerous tissue, a comparable level of expression of 9-cis-retinol dehydrogenase indicating a predisposition to cancer in the subject.

As used herein a subject may be any animal, preferably a mammal, and most preferably a human.

This invention provides a method for detecting a predisposition to a cancer or to a disease associated with the either an overexpression or an underexpression of a human 9-cis-retinol dehydrogenase in a sample from a subject which comprises: a) obtaining DNA from the sample of the subject suffering from cancer or from the disease associated with either an overexpression or an underexpression of a human 9-cis-retinol dehydrogenase; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; e) detecting labeled DNA fragments which have hybridized to the nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase creates a unique band pattern specific to the DNA of subjects suffering from cancer; f) preparing DNA obtained from a sample of a subject for diagnosis by steps (a–e); and g) comparing the detected band pattern specific to the DNA obtained from a sample of subjects suffering from cancer or from the disease associated with either an overexpression or an underexpression of a human 9-cis-retinol dehydrogenase from step (e) and the DNA obtained from a sample of the subject for diagnosis from step (f) to determine whether the patterns are the same or different and to diagnose thereby predisposition to the cancer or the disease associated with the overexpression or the underexpression of the human 9-cis-retinol dehydrogenase if the patterns are the same.

In an embodiment of the above-described methods for detecting a predisposition to a cancer or to a disease associated with either an overexpression or an underexpression of a human 9-cis-retinol dehydrogenase in a sample from a subject, the size fractionation in step (c) is effected by a polyacrylamide or agarose gel. In another embodiment of the above-described method, the detectable marker is radioactive isotope, enzyme, dye, biotin, a fluorescent label or a chemiluminescent label.

This invention provides a method for detecting a predisposition to a cancer or to a disease associated with an overexpression of a human 9-cis-retinol dehydrogenase in a sample from a subject which comprises: a) obtaining DNA from the sample of the subject suffering from cancer or from the disease associated with an overexpression of a human 9-cis-retinol dehydrogenase; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; e) detecting labeled DNA fragments which have hybridized to the nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase creates a unique band pattern specific to the DNA of subjects suffering from cancer; f) preparing DNA obtained from a sample of a subject for diagnosis by steps (a–e); and g) comparing the detected band pattern specific to the DNA obtained from a sample of subjects suffering from the cancer or from the disease associated with the overexpression of a human 9-cis-retinol dehydrogenase from step (e) and the DNA obtained from a sample of the subject for diagnosis from step (f) to determine whether the patterns are the same or different and to diagnose thereby predisposition to the cancer or the disease associated with the overexpression of the human 9-cis-retinol dehydrogenase if the patterns are the same.

This invention provides a method for detecting a predisposition to a cancer or to a disease associated with an underexpression of a human 9-cis-retinol dehydrogenase in a sample from a subject which comprises: a) obtaining DNA from the sample of the subject suffering from cancer or from the disease associated with an underexpression of a human 9-cis-retinol dehydrogenase; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; e) detecting labeled DNA fragments which have hybridized to the nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase creates a unique band pattern specific to the DNA of subjects suffering from cancer; f) preparing DNA obtained from a sample of a subject for diagnosis by steps (a–e); and g) comparing the detected band pattern specific to the DNA obtained from a sample of subjects suffering from cancer or from the disease associated with the underexpression of a human 9-cis-retinol dehydrogenase from step (e) and the DNA obtained from a sample of the subject for diagnosis from step (f) to determine whether the patterns are the same or different and to diagnose thereby predisposition to the cancer or the disease associated with the underexpression of the human 9-cis-retinol dehydrogenase if the patterns are the same.

In an embodiment of the above-described methods for detecting a predisposition to a cancer or to a disease associated with either an overexpression or an underexpression of a human 9-cis-retinol dehydrogenase in a sample from a subject, the size fractionation in step (c) is effected by a polyacrylamide or agarose gel. In another embodiment of the above-described method, the detectable marker is radioactive isotope, enzyme, dye, biotin, a fluorescent label or a chemiluminescent label.

This invention provides a method for detecting a predisposition to a cancer or a disease associated with the overexpression or under expression of a human 9-cis-retinol dehydrogenase in a sample from a subject which comprises: a) obtaining RNA from the sample of the subject suffering from the cancer or the disease associated with the overexpression or under expression of the human 9-cis-retinol dehydrogenase; b) separating the RNA sample by size fractionation; c) contacting the resulting RNA species with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; d) detecting labeled bands which have hybridized to the RNA species to create a unique band pattern specific to the RNA of subjects suffering from the cancer or the disease associated with the overexpression or under expression of the human 9-cis-retinol dehydrogenase; e) preparing RNA obtained from a sample of a subject for diagnosis by steps (a–d); and f) comparing the detected band pattern specific to the RNA obtained from a sample of subjects suffering from the cancer or the disease associated with the overexpression or under expression of a human 9-cis-retinol dehydrogenase from step (d) and the RNA obtained from a sample of the subject for diagnosis from step (f) to determine whether the patterns are the same or different and to diagnose thereby predisposition to the cancer or the disease associated with the overexpression or underexpression of the human 9-cis-retinol dehydrogenase if the patterns are the same.

In an embodiment of the above-described methods for detecting a predisposition to a cancer or to a disease associated with either an overexpression or an underexpression of a human 9-cis-retinol dehydrogenase in a sample from a subject, the size fractionation in step (c) is effected by a polyacrylamide or agarose gel. In another embodiment of the above-described method, the detectable marker is radioactive isotope, enzyme, dye, biotin, a fluorescent label or a chemiluminescent label. In a further embodiment of any of the above-described methods for detecting a predisposition to a cancer or a disease associated with the overexpression or under expression of a human 9-cis-retinol dehydrogenase in a sample from a subject, the cancer or the disease associated with the overexpression or underexpression of the human 9-cis-retinol dehydrogenase is diagnosed.

This invention provides an antisense oligonucleotide having a sequence capable of specifically hybridizing to an mRNA molecule encoding a human 9-cis-retinol dehydrogenase so as to prevent expression of the mRNA molecule. In an embodiment the antisense oligonucleotide has a sequence capable of specifically hybridizing to the isolated cDNA molecule encoding a mammalian 9-cis-retinol dehydrogenase. In another embodiment the antisense oligonucleotide has a sequence capable of specifically hybridizing to the isolated genomic DNA molecule encoding a mammalian 9-cis-retinol dehydrogenase. In an embodiment the antisense oligonucleotide has a sequence capable of specifically hybridizing to the isolated RNA molecule encoding a mammalian 9-cis-retinol dehydrogenase.

As used herein, the phrase "specifically hybridizing" means the ability of a nucleic acid molecule to recognize a nucleic acid sequence complementary to its own and to form double-helical segments through hydrogen bonding between complementary base pairs. As used herein, a "unique sequence" is a sequence specific to only the nucleic acid molecules encoding the 9-cis-retinol dehydrogenase protein. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid molecules encoding the 9-cis-retinol dehydrogenase protein is useful as a diagnostic test for any disease process in which levels of expression of the corresponding 9-cis-retinol dehydrogenase protein is altered. DNA probe molecules are produced by insertion of a DNA molecule which encodes mammalian 9-cis-retinol dehydrogenase protein or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIGS. 1A–1B and 4A–4G. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a mammalian 9-cis-retinol dehydrogenase protein, e.g. human 9-cis-retinol dehydrogenase are useful as probes for this gene, for its associated mRNA, or for the isolation of related genes by homology screening of genomic or cDNA libraries, or by the use of amplification techniques such as the Polymerase Chain Reaction.

A preferred embodiment of a nucleic acid molecule probe of a mammalian 9-cis-retinol dehydrogenase protein is a DNA molecule probe.

This invention provides a purified 9-cis-retinol dehydrogenase, wherein the 9-cis-retinol dehydrogenase is a human 9-cis-retinol dehydrogenase.

This invention provides an antibody directed to a purified 9-cis-retinol dehydrogenase or to a purified 9-cis-retinol dehydrogenase, wherein the 9-cis-retinol dehydrogenase is a human 9-cis-retinol dehydrogenase.

This invention provides an antibody capable of specifically recognizing 9-cis-retinol dehydrogenase. In an embodiment the antibody may be a polyclonal antibody. In another embodiment the antibody may be a monoclonal antibody.

This invention provides an antibody capable of specifically recognizing unique amino acid residues of 9-cis-retinol dehydrogenase. In a preferred embodiment of the antibody the unique amino acid residues of 9-cis-retinol dehydrogenase are HYGGAFLKYLKMQQRIMNLI (SEQ ID NO: 9).

Polyclonal antibodies may be produced by injecting a host animal such as rabbit, rat, goat, mouse or other animal with the immunogen of this invention. The sera are extracted from the host animal and are screened to obtain polyclonal antibodies which are specific to the immunogen. Methods of screening for polyclonal antibodies are well known to those of ordinary skill in the art such as those disclosed in Harlow & Lane, *Antibodies: A Laboratory Manual*, (Cold Spring Harbor Laboratories, Cold Spring Harbor, N.Y.: 1988) the contents of which are hereby incorporated by reference.

The monoclonal antibodies may be produced by immunizing for example, mice with an immunogen. The mice are inoculated intraperitoneally with an immunogenic amount of the above-described immunogen and then boosted with similar amounts of the immunogen. Spleens are collected from the immunized mice a few days after the final boost and a cell suspension is prepared from the spleens for use in the fusion.

Hybridomas may be prepared from the splenocytes and a murine tumor partner using the general somatic cell hybridization technique of Kohler, B. and Milstein, C., Nature (1975) 256: 495–497. Available murine myeloma lines, such as those from the American Type Culture Collection (ATCC) 12301 Parklawn Drive, Rockville, Md. 20852 USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures, for example radioimmunoassay, using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

In the practice of the subject invention any of the above-described antibodies may be labeled with a detectable marker. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. A "detectable moiety" which functions as detectable labels are well known to those of ordinary skill in the art and include, but are not limited to, a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin. Methods of labeling antibodies are well known in the art.

This invention provides a method of detecting expression of a mammalian 9-cis-retinol dehydrogenase in a tissue or cells from a sample which comprises: a) incubating a sample of the tissue or cells from a sample with an antibody which specifically recognizes 9-cis-retinol dehydrogenase and is labeled with a detectable marker under conditions permitting a binding of the antibody to the tissue or the cells; b) detecting labeled tissue or cells, thereby detecting expression of the mammalian 9-cis-retinol dehydrogenase in the tissue or the cells.

As used herein, "sample" means body tissue or fluid, including but not limited to blood, urine, saliva, and cerebrospinal fluid.

This invention provides a method of detecting human 9-cis-retinol dehydrogenase in a sample which comprises: a) contacting the sample with of any of the above-described antibodies under conditions permitting the formation of a complex between the antibody and the human 9-cis-retinol dehydrogenase in the sample; and b) detecting the complex formed in step (a) thereby detecting the presence of human 9-cis-retinol dehydrogenase in the sample. In an embodiment the antibody is labeled with a detectable marker. In an embodiment the the detectable marker is radioactive isotope, enzyme, dye, biotin, a fluorescent label or a chemiluminescent label.

This invention provides a method of detecting a disease which is responsive to treatment with a retinoid, comprising the method of detecting human 9-cis-retinol dehydrogenase in a tissue or cells from a sample, wherein the detection of the expression of the mammalian 9-cis-retinol dehydrogenase indicates the disease is responsive to retinoic acid treatment.

This invention provides a method of detecting a disease which is refractory to treatment with a retinoid comprising the method of detecting human 9-cis-retinol dehydrogenase in a tissue or cells from a sample, wherein the detection of the expression of the mammalian 9-cis-retinol dehydrogenase indicates the disease is refractory to retinoic acid treatment.

This invention provides a pharmaceutical composition comprising an amount of any of the above-described oligonucleotides and effective to prevent overexpression of a human 9-cis-retinol dehydrogenase and a pharmaceutically acceptable carrier capable of passing through a cell membrane.

This invention provides a pharmaceutical composition comprising an amount of any compounds, e.g. retinoids, which are determined to be potentially therapeutic, i.e. their toxicity as determined by any of the methods described supra is less than that of compounds which in a smaller concentration have a higher toxicity, administered in effective amounts and a pharmaceutically acceptable carrier capable of passing through a cell membrane.

This invention provides a method of administering the above-described pharmaceutical composition comprising an amount of any of the above-described oligonucleotides or compounds which are determined to be potentially therapeutic, wherein the administration is intravenous, intraperitoneal, intrathecal, intralymphatical, intramuscular, intralesional, parenteral, epidural, subcutaneous; by infusion, liposome-mediated delivery, aerosol delivery; topical, oral, nasal, anal, ocular or otic delivery.

The present invention also provides a pharmaceutical composition comprising a effective amount of any of the above-described oligonucleotides or compounds which are determined to be potentially therapeutic and a pharmaceutically acceptable carrier. In the subject invention an "effective amount" is any amount of the above-described oligonucleotides or compounds which are determined to be potentially therapeutic, which, when administered to a subject suffering from a disease or abnormality against which the above-described oligonucleotides or compounds which are determined to be potentially therapeutic, are effective, causes reduction, remission, or regression of the disease or abnormality. In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The above-described oligonucleotides or compounds which are determined to be potentially therapeutic can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The above-described oligonucleotides or compounds which are determined to be potentially therapeutic can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular oligonucleotide in use, the strength of the preparation, the mode of administration, and the advancement of the disease condition or abnormality. Additional factors depending on the particular subject being treated will result in a need to adjust dosages, including subject age, weight, gender, diet, and time of administration.

This invention provides a recombinant non-human vertebrate animal wherein the functional 9-cis-retinol dehydrogenase is not expressed. In an embodiment the recombinant non-human vertebrate animal is a rodent. In a preferred embodiment the rodent is a mouse.

This invention provides a recombinant non-human vertebrate animal wherein the functional 9-cis-retinol dehydrogenase is underexpressed. In an embodiment the recombinant non-human vertebrate animal is a rodent. In a preferred the rodent is a mouse.

This invention provides a method of treating any of the above-described recombinant non-human vertebrate animals comprising administration of a vector comprising an isolated mammalian nucleic acid molecule encoding a 9-cis-retinol dehydrogenase.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

First Series of Experiments

All-trans- and 9-cis-retinoic acid are active retinoids for regulating expression of retinoid responsive genes, serving as ligands for two classes of ligand-dependent transcription factors, the retinoic acid receptors and retinoid X receptors. Little is known, however, regarding 9-cis-retinoic acid formation. We have obtained a 1.4-kilobase cDNA clone from a normalized human breast tissue library, which when expressed in CHO cells encodes a protein that avidly catalyzes oxidation of 9-cis-retinol to 9-cis-retinaldehyde. This protein also catalyzes oxidation of 13-cis-retinol at a rate approximately 10% of that of the 9-cis isomer but does not catalyze all-trans-retinol oxidation. NAD+ was the preferred electron acceptor for oxidation of 9-cis-retinol, although NADP+ supported low rates of 9-cis-retinol oxidation. The rate of 9-cis-retinol oxidation was optimal at pHs between 7.5 and 8. Sequence analysis indicates that the cDNA encodes a protein of 319 amino acids that resembles members of the short chain alcohol dehydrogenase protein family. mRNA for the protein is most abundant in human mammary tissue followed by kidney and testis, with lower levels of expression in liver, adrenals, lung, pancreas, and skeletal muscle. We propose that this cDNA encodes a previously unknown stereospecific enzyme, 9-cis-retinol dehydrogenase, which probably plays a role in 9-cis-retinoic acid formation.

Retinoids (vitamin A and its analogs) are essential dietary substances that are needed by mammals for reproduction, normal embryogenesis, growth, vision, and maintaining normal cellular differentiation and the integrity of the immune system (1–5). Within cells, retinoids regulate gene transcription acting through ligand-dependent transcription factors, the retinoic acid receptors (RARs)[1], and the retinoid X receptors (RXRS) (6,7). All-trans-retinoic acid binds only to RARs with high affinity, whereas its 9-cis isomer binds with high affinity to both RARs and RXRs. The actions of all-trans- and 9-cis-retinoic acid in regulating cellular responses are distinct and not interchangeable.

In contrast to the great explosion of information regarding the actions of retinoid receptors in regulating gene transcription, information regrading how the abundant precursor retinol is physiologically activated to form the ligands needed to activate retinoid receptors is only slowly emerging (see Refs. 8 and 9 for recent reviews). It is clear that the pathway for conversion of retinol to retinoic acid involves first the oxidation of retinol to retinaldehyde and then the oxidation of retinaldehyde to retinoic acid. Numerous enzymes that are able to catalyze either retinol or retinaldehyde oxidation have been identified, purified, and/or characterized (8–10). These enzymes are members of four distinct families: the alcohol dehydrogenases, the short chain alcohol dehydrogenases, the aldehyde dehydrogenases, and cytochrome P-450s (8–10). At present, the most attention has focused on enzymes responsible for the oxidation of all-trans-retinol to all-trans-retinaldehyde (11–15). Several recent reports have indicated that both alcohol dehydrogenases and short chain alcohol dehydrogenases may be responsible for catalyzing all-trans-retinol oxidation (11–15), but the exact in vivo roles of each of these dehydrogenases in all-trans-retinoic acid formation remains controversial (8).

9-cis-Retinoic acid has been reported to be present in mammalian tissues and cells (16–18), but it has not been convincingly established how 9-cis-retinoic acid is formed within tissues and cells. Urbach and Rando have reported that liver microsomes can nonenzymatically catalyze the isomerization of all-trans-retinoic acid to the 9-cis isomer (19). Others have demonstrated that 9-cis-β-carotene can be converted to 9-cis-retinoic acid within rat tissues (20). However, this latter pathway cannot be an essential one for 9-cis-retinoic acid formation because rats maintained on a β-carotene-free purified diet containing only retinol as a precursor for retinoic acid formation are normal. In this communication, we report the characterization of a cDNA clone for a novel human enzyme that we have designated 9-cis-retinol dehydrogenase (9cRDH) and that catalyzes in a stereospecific manner the oxidation of 9-cis-retinol to 9-cis-retinaldehyde, a first enzymatic step needed for 9-cis-retinoic acid formation. Because it has been established that 9-cis-retinaldehyde can be further oxidized to 9-cis-retinoic acid by abundant tissue retinaldehyde dehydrogenases (21–23), it is possible that 9cRDH catalyzes a key oxidation step in the formation of 9-cis-retinoic acid.

EXPERIMENTAL PROCEDURES cDNA Characterization and Sequence Analysis. Using a primer homology strategy based on sequence information provided by Napoli and colleagues (11–14), we screened a mouse testis library for a retinol dehydrogenase cDNA clone We obtained a 550-bp cDNA that we submitted for automated DNA sequence analysis (ABI Applied Biosystems, model 373A, Columbia, Md.) through the Columbia University Comprehensive Cancer Center Core DNA Sequencing Facility. When this partial cDNA sequence was compared with sequences that had been deposited in GenBank™ (National Center for Biotechnology Information, Bethesda, Md.), a very high degree of sequence homology was observed with an unidentified cDNA sequence that had been partially sequenced (330 of approximately 1400 bp) and deposited with GenBank™ by the IMAGE Consortium (accession number R50456). We obtained the cDNA through Research Genetics, Inc (Huntsville, Ala.), and its complete nucleotide sequence was determined. The 1.4-kb cDNA was subcloned so that overlapping sequences were obtained for all regions of the cDNA and was used for all studies reported below Expression of 9-cis-Retinol Dehydrogenase. The 1.4-kb human cDNA was directionally cloned as a BamHI-EcoRI insert into the mammalian expression vector pcDNA3 (Invitrogen, San Diego, Calif.) where expression is driven by the strong promoter from the immediate early gene of the human cytomegalovirus. Both the expression vector containing the cDNA insert and vector alone were transfected using calcium phosphate into CHO cells according to standard procedures (24). Routinely, 20 µg of plasmid DNA (with or without the cDNA insert) was transfected into $2 \times 10_6$ CHO cells maintained on 100-mm tissue culture plates. At the time of transfection, the CHO cells were approximately 80~o confluent. 27 h after transfection, the transfection medium was removed from the CHO cells, and they were washed with 5 ml of ice-cold 10 mM sodium phosphate, 150 mM NaCl, pH 7.4 (PBS). Washed CHO cells were scraped from the plate and collected by centrifugation at 500×g at 4° C. for 10 min. The pelleted cells were washed with 5 ml of ice-cold PBS two additional times and stored as a cell pellet at −20° C. for up to 2 weeks prior to assay for retinol dehydrogenase activity.

Retinoids. All-trans-retinol was obtained as a gift from Dr. Christian Eckhoff of Hoffmann-LaRoche, Inc. (Nutley, N.J.), and 13-cis-retinol was purchased from Sigma. 9-cis- Retinol was synthesized by NaBH$_4$ reduction of authentic 9-cis-retinaldehyde (Sigma) and subsequently purified by normal phase HPLC essentially as we have described for 11-cis-retinol synthesis and purification (25). All-trans-, 13-cis-, and 9-cis-retinaldehydes were purchased from Sigma.

Enzymatic Assay of Retinol Dehydrogenase Activity. Transfected CHO cell pellets were homogenized in PBS at 4° C. using 50 strokes of a Dounce homogenizer For assay of retinol dehydrogenase activity, aliquots of unfractionated CHO cell homogenate were incubated with 10 μM retinol (either as the all-trans, 13-cis, or 9-cis isomer added in ethanol) and either 2 mM NAD+ or 2 mM NADP+ in 10 mM Hepes containing 150 mM KCl, 1 mM EDTA, and 10 μg/ml phosphotidyl choline at pH 8.0 and 37° C. for prechosen time intervals. The final assay volume was 0.6 ml. Assays were routinely carried out in amber glass tubes that had been flushed with N$_2$ to shield the retinoids from both light and O$_2$ All subsequent extractions and procedures were carried out in a manner that minimized exposure of the retinoids to light and O$_2$.

Immediately following incubation, the assay mixture was denatured with an equal volume of absolute ethanol (0.6 ml), and the retinoids were extracted into 3 ml of HPLC grade hexane. Following one backwash of the hexane extract with 0.5 ml of deionized water, the hexane was evaporated to dryness under a gentle stream of N$_2$, and the extracted retinoids were immediately redissolved in 120 μl of hexane and analyzed by normal phase HPLC (see below).

For assay of 9cRDH activity in rat tissues, 300-g male Sprague-Dawley rats were sacrificed in a CO$_2$-saturated atmosphere and liver, kidney, spleen, testis, and epididymis were quickly removed and placed on ice. Immediately after dissection, each tissue was finely minced with razor blades, placed into a Dounce homogenizer containing 4 volumes of ice-cold PBS and homogenized with 50 strokes of the homogenizer. The resulting homogenate was centrifuged at 500×g for 10 min to remove debris and was maintained on ice prior to its use for 9cRDH assay. Assays of 9cRDH activity were carried out exactly as described above for CHO cell homogenates. For each assay, a blank containing substrate and homogenate was maintained on ice for 1 h and was subsequently extracted to correct for possible endogeneous 9-cis-retinaldehyde presence in the enzyme sources; however, in no homogenate was any 9-cis-retinaldehyde observed.

The protein concentrations of CHO cell homogenates and of each homogenate from the rat tissues were determined using the Bradford reagent (Pierce) according to the manufacturer's instructions.

HPLC Procedures. Stereoisomers of both retinol and retinaldehyde were separated on a 4.6×250-mm Vydac 101HS54 silica column using hexane:n-propanol:1-octanol (98.9:1.0:0.1 v/v) flowing at 1.5 ml/min as the mobile phase. The running column was preceded by a silica guard column. Retinols and retinaldehydes were detected by UV absorbance at 350 nm. Retention times for all-trans-, 13-cis-, and 9-cis-retinols were established using purified compounds obtained as described above. Retention times for all-trans-, 13-cis-, and 9-cis-retinaldehyde were determined using commercial standards (Sigma). Quantities of each retinol and retinaldehyde isomer present in extracts were determined by comparisons of the integrated areas under the HPLC peaks with a standard curve constructed relating integrated peak area with known masses of each retinoid isomer. The concentrations of each retinoid isomer were determined by UV-visible spectrophotometry using published extinction coefficients for each retinol and retinaldehyde isomer (26).

Northern Blot Analysis for 9cRDH Expression in Human Tissues. Northern blot analysis was used to explore 9cRDH expression in human testis, kidney, lung, liver, heart, adrenals, pancreas, thyroid, skeletal muscle, placenta, mammary gland, and a mammary tumor. All tissues, with the exception of mammary gland and mammary tumor, were obtained at autopsy. The mammary gland and mammary tumor were obtained as frozen blocks embedded for diagnosis. Total RNA was isolated from each tissue sample using standard procedures (24). Total RNA samples were electorphoresed on 0.8% agarose containing 2.2 M formaldehyde at 0.5 V/cm for 14 h. After electrophoresis the gel was soaked in 20×SSC for 1 h and blotted overnight onto a nitrocellulose membrane using 10×SSC. The total RNA transferred to the nitrocellulose membrane was baked at 80° C. in a vacuum oven for 2 h. The blot was probed with a cRNA probe generated from the full-length human 9cRDH cDNA clone in pcDNA3 (as used for CHO cell expression studies). The cRNA probe was labeled using SP6 polymerase and [$^{32}$P] UTP. Hybridization was carried out at 65° C. in 5×SSC, 60% formamide, 1% SDS, 5×Denhardt's solution, 100 μg/ml salmon sperm DNA, 100 μg/ml yeast tRNA, and 7% dextran sulfate. After hybridization, the final wash f the RNA-RNA blot was at 80° C. in 0.2×SSC and 0.1% SDS for 1 h.

EXPERIMENTAL RESULTS

We were interested in obtaining a cDNA clone for a retinol dehydrogenase from a mouse testis library for use in study of the cellular sites of retinoic acid formation within the testis. Using a primer homology strategy similar to strategies described by Napoli and colleagues (11–14), we obtained a partial length product (550 bp) which, upon search of known sequences present in GenBank™, was found to have a very high sequence homology to a previously unidentified cDNA having a length of 1.4 kb and for which a partial sequence had been obtained as part of the Human Genome Project. Because this cDNA was much larger than the one we obtained from the screen of the mouse testis library, we obtained the cDNA for preliminary study. Our preliminary characterizations of this human cDNA suggested to us that the cDNA encoded a protein that could catalyze the reduction of NAD+ when a mixture of retinol isomers was incubated with expressed protein encoded by the cDNA; consequently, we set out to characterize more extensively this human cDNA and the protein that it encodes.

Because only 330 bp of the approximately 1400 bp present in the human cDNA had been sequenced, we completed the sequencing of this cDNA. The complete nucleotide sequence for the cDNA is provided in FIG. 1 along with the deduced amino acid sequence for the protein that it encodes. Sequence analysis of the cDNA revealed the presence of a putative translation start site approximately 80 bp downstream from its 5'-end and continuing for approximately 170 bp after the occurrence of a translation stop codon. The cDNA consisted of 1239 bp and could encode a protein of 319 amino acids. A search of the GenBank™ for homologous sequences indicated that bovine retinal pigment epithelial 11-cis-retinol dehydrogenase and rat liver all-trans-retinol dehydrogenases, types I, II, and III, were highly homologous to that of the 1.4-kb cDNA. For comparison, the deduced amino acid sequences for bovine 11-cis-retinol dehydrogenase and rat all-trans-retinol dehydrogenases, types I and II, are also provided in FIG. 1. No other sequences present in the GenBank™ data base were similarly homologous to the sequence that we obtained. Computer analysis of the predicted amino acid sequence indicated that the protein contained no membrane spanning domains. Furthermore, computer analysis of the amino acid sequences indicated that the protein encoded by the cDNA clone is most probably a member of the family of short chain alcohol dehydrogenases, like the bovine 11-cis-retinol dehydrogenase (27, 28) and the rat liver retinol dehydrogenases, types I, II, and III (11–14).

Based on these sequence homologies and the results from our preliminary studies, it seemed likely to us that we had obtained a human cDNA clone for a retinol dehydrogenase. However, based on our preliminary studies, it was not fully clear whether this cDNA was a human homolog of one of the rat liver all-trans-retinol dehydogenases (11–14) or whether we had cloned a new and previously undescribed retinol dehydrogenase. Because 11-cis-retinol dehydrogenase is expressed only in the retinal pigment epithelium (27, 28) and 11-cis-retinol is found only in the eye (4), we could not have cloned the human homolog for this enzyme. To determine the substrate specificity of the enzyme encoded by our cDNA, we expressed the cDNA in CHO cells and incubated homogenate from these CHO cells with all-trans-, 9-cis-, or 13-cis-retinol. As is seen in FIG. 2, in the presence of 2 mM NAD+, homogenate from the transfected CHO cells avidly oxidized 9-cis-retinol to 9-cis-retinaldehyde but was unable to catalyze the oxidation of all-trans-retinol to all-trans-retinaldehyde. The CHO cell homogenate catalyzed the oxidation of 13-cis-retinol to its corresponding aldehyde, but at a rate that was only 10% of that observed for the oxidation of 9-cis-retinol. Over 60% of the 9-cis-retinol added (at an in assay concentration of 10 $\mu$M) could be oxidized to 9-cis-retinaldehyde by the CHO cell homogenate. Oxidation of 9-cis-retinol was both protein- and time-dependent, and NADP+ was a poor co-factor for the reaction (8% of the activity of NAD+ when both are provided at concentrations of 2 mM) The CHO cell homogenates were unable to catalyze any detectable oxidation of all-trans-retinol, regardless of whether this retinoid was added to the CHO homogenate in organic solvents, bound to rat testis cellular retinol-binding protein, type I, bound to albumin, or in detergent emulsions. We conclude from these experiments that the 1.4-kb cDNA encodes a stereospecific 9-cis-retinol dehydrogenase (9cRDH) that has not been previously identified.

Further characterization of 9cRDH activity expressed in CHO cells indicated that the enzyme has a pH optimum in the range of 7.5–8.0 and that 9cRDH activity is not inhibited by ethanol or zinc chelators like EDTA or o-phenanthroline, unlike cytosolic alcohol dehydrogenases that can oxidize retinol to retinaldehyde (15, 29) Neither exposure to high NaCl concentrations (up to 1 M) nor exposure to reducing reagents (1 mM ,$\beta$-mercaptoethanol and 1 mM dithiothreitol) influenced 9cRDH activity. CHO cell expressed 9cRDH activity, however, is sensitive to detergents and is rapidly inactivated by exposure to 1% (w/v) Triton X-100 or to 1% (w/v) sodium cholate. In addition, the 9cRDH activity present in CHO cell homogenates is rapidly lost upon storage at −20° C., although the activity does not appear to be lost when CHO cells are frozen intact.

Figure 3:
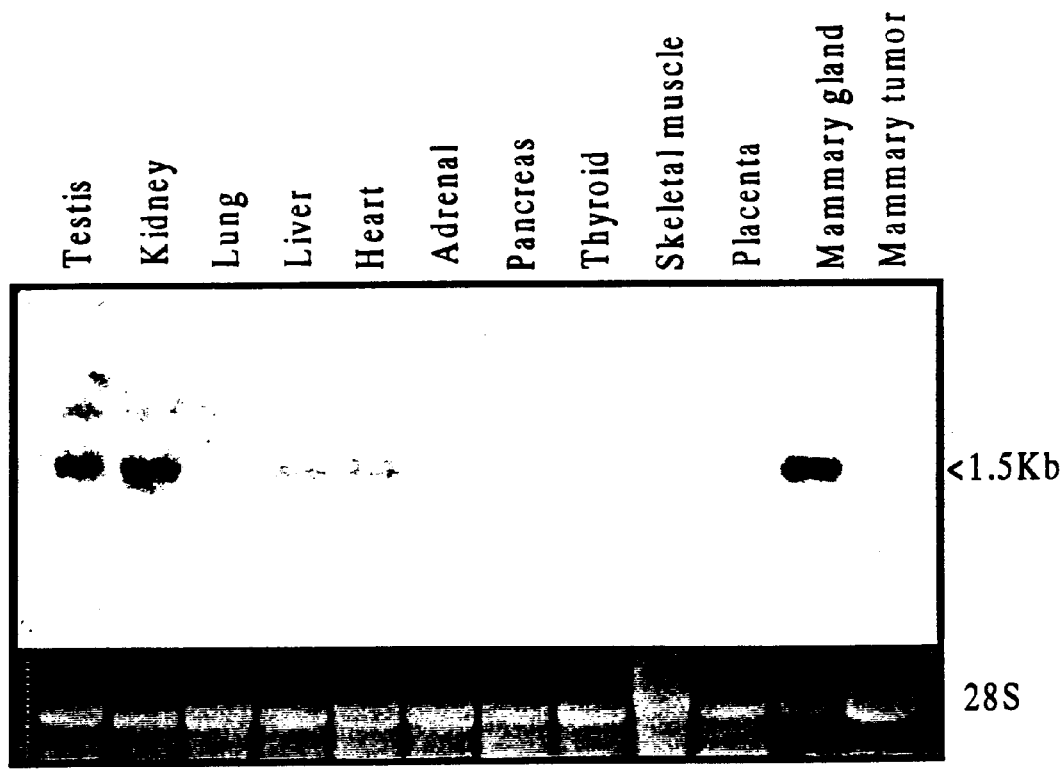
FIG. 3. Northern blot analysis of 9cRDH expression in human testis, kidney, lung, liver, heart, adrenals, pancreas, thyroid, skeletal muscle, placenta, mammary gland, and mammary tumor. All tissues, with the exception of placenta, mammary gland and mammary tumor were obtained at autopsy. The mammary gland and mammary tumor were obtained as frozen blocks embedded for diagnosis, and term placenta was obtained as the intact tissue. This analysis was carried out as described under "Experimental Procedures" with 50 µg of total RNA loaded in each lane except for mammary gland where only 20 µg of total RNA was loaded.

The distribution of 9cRDH expression in human tissues was assessed by Northern blot analysis (FIG. 3) The transcript identified by Northern blot analysis is approximately 1.5 kb, a size that agrees well with that predicted by the full-length human 9cRDH cDNA clone. 9cRDH mRNA is most abundant in normal mammary tissue and is relatively abundant in kidney and the testis. Liver, heart, and adrenals each express 9cRDH mRNA at nearly equal levels, but these are lower than those of mammary tissue, kidney and testis. 9cRDH mRNA is present at low levels in lung, pancreas, and skeletal muscle. Interestingly, 9cRDH is only very weakly expressed in total RNA prepared from a human mammary tumor. We also asked whether 9cRDH activity could be detected in whole tissue homogenates prepared from rat liver, spleen, kidney, epididymis, and testis. As shown in Table I, 9cRDH specific activity was highest in the kidney followed by the testis, epididymis, liver, and spleen.

TABLE I

Specific activity levels of 9-cis-Retinol dehydrogenase in selected rat tissue homogenates

| Tissue | 9-cis-Retinaldehyde formed nmol/h/mg protein |
| --- | --- |
| Liver | 2.4 ± 0.4[a] |
| Kidney | 4.9 ± 0.1 |
| Spleen | 1.6 ± 0.3 |
| Testis | 3.6 ± 0.5 |
| Epididymis | 2.8 ± 1.0 |

[a]Values are expressed as the means ± S.D. for activity determinations for homogenates prepared from tissues from three animals

EXPERIMENTAL DISCUSSION

It is generally accepted that 9-cis-retinoic acid is a hysiologically important molecule for mediating retinoid actions in regulating gene expression, but only limited information has been available regarding how 9-cis-retinoic acid or any 9-cis-retinoid is formed within tissues and cells. This is unlike the visual process where it is now well established that isomerization of all-trans-retinoids to 11-cis-retinoids is catalyzed by a specific enzyme and that the isomerization takes place at the level of the retinols and not the retinaldehydes (4). Because of the first reports in 1992 that 9-cis-retinoic acid is a ligand for the RXRs, several studies have explored possible pathways for 9-cis-retinoic acid formation. Urbach and Rando have reported that membranes prepared from bovine liver will catalyze non-enzymatically the isomerization of all-trans-retinoic acid to 9-cis-retinoic acid (19). This isomerization was shown to depend on free sulfhydryl groups present in the microsomes and not to involve the participation of an enzyme (19). Krinsky, Russell, and colleagues have reported that 9-cis-$\beta$-carotene serves as a precursor for 9-cis-retinoic acid in vivo in the rat (20) However, because rats maintained on carotenoid-free diets display normal health, the conversion of 9-cis-$\beta$-carotene to 9-cis-retinoic acid cannot be an essential pathway for formation of this retinoic acid isomer. In studies of retinaldehyde dehydrogenases purified from rat kidney (21, 22) and rat liver (23), the ability of these enzymes to catalyze the oxidation of 9-cisretinaldehyde to 9-cis-retinoic acid was taken to suggest that a pathway starting with 9-cis-retinol may be important for 9-cis—retinoic acid formation (21, 22). To further substantiate this possibility, Bhat, Lacroix, and colleagues demonstrated the presence of 9-cis-retinol in rat kidney at levels that were approximately 10% of that of all-trans-retinol (22). Our work characterizing a stereospecific 9cRDH activity and demonstration of the broad tissue distribution of this enzyme adds additional support to the hypothesis that 9-cis-retinoic acid is formed within tissues via a pathway that involves both 9-cis-retinol and 9-cis-retinaldehyde.

A search of the GenBank™ for DNA sequences homologous to that of 9cRDH revealed that the sequence of the 9cRDH cDNA is approximately 87% homologous to that of the full-length cDNA for bovine retinal pigment epithelium il-cis-retinol dehydrogenase (27) and approximately 48% homologous to the coding region of the cDNA sequence for rat liver all-trans—retinol dehydrogenase, type II (13). At the amino acid level, the deduced amino acid sequence for 9cRDH is 89% identical to that of bovine il-cis-retinol dehydrogenase (27) and 53% identical to that of rat liver all-trans-retinol dehydrogenase, type II (13). Like the bovine 11-cis-retinol dehydrogenase and the rat liver all-trans-retinol dehydrogenases, types I, II, and III, 9cRDH is a member of the family of short chain alcohol dehydrogenases. Moreover, 9cRDH shares many properties including pH optimum, insensitivity to inhibition by ethanol, and sensitivity to detergent inactivation with the other members of this protein family. Most importantly though, like these other short chain alcohol dehydrogenases, 9cRDH shows a marked stereospecificity for retinol substrates.

Based on work showing that a retinaldehyde dehydrogenase purified from rat kidney can catalyze the oxidation of both all-trans- and 9-cis-retinaldehyde and that 9-cis-retinol is present in relatively high levels in the rat kidney (21, 22), it has been hypothesized that 9-cis-retinoic acid is formed in the kidney through a two-step oxidation starting with 9-cis-retinol. The demonstration of 9cRDH in the kidney provides strong support for this hypothesis. Moreover, identification of this short chain alcohol dehydrogenase, 9cRDH, raises many additional interesting questions regarding the biochemical processes that are important for providing 9-cis-retinoids to tissue and cell. One such question concerns how 9-cis-retinoids are formed. Whether or not isomerization of all-trans-retinoic acid actually occurs nonenzymatically in living cells has not been addressed experimentally, although it is clear that some cell types do have the capacity to isomerize all-trans-retinoic acid to the 9-cis isomer (30). Another important question regarding 9-cis-retinoid formation concerns whether there are other short chain alcohol dehydrogenases present in tissues and cells distinct from 9cRDH that catalyze 9-cis-retinol oxidation. There are at least three short chain alcohol dehydrogenases that catalyze all-trans-retinol oxidation (11–14), and it would not seem unreasonable that multiple forms of 9cRDH may also exist. Perhaps most importantly, though, it is essential to gain an understanding of the specific physiologic role or roles played by each of these short chain alcohol dehydrogenases and by each of the alcohol dehydrogenases that catalyze oxidation of retinol to retinaldehyde. These enzymes may be redundant or they all may play significant roles in retinoic acid formation in specific and defined cellular and metabolic contexts. Although it is clear that many enzymes are able to catalyze retinol oxidation, convincing physiologic functions for these enzymes within living organisms remain elusive.

REFERENCES FOR FIRST SERIES OF EXPERIMENTS

1. Wolbach, S. B., and Howe, P. R. (1925) J. Exp. Med. 42, 753–778.
2. Gudas, L. J., Sporn, M. B., and Roberts, A. B. (1994) in The Retinoids, Biology, Chemistry, and Medicine (Sporn, M. B., Roberts, A. B., and Goodman, D. S., eds) pp. 443–520, Raven Press, New York.
3. Hofmann, C., and Eichele, G. (1994) in The Retinoids, Biology, Chemistry, and Medicine (Sporn, M. B., Roberts, A. B., and Goodman, D. S., eds) pp. 387–441, Raven Press, New York.
4. Saari, J. C. (1994) in The Retinoids, Biology, Chemistry, and Medicine (Sporn, M. B., Roberts, A. B, and Goodman, D. S., eds) pp. 351–386, Raven Press, New York.
5. Ross A. C., and Hammerling, U. L. (1994) in The Retinoids, Biology, Chemistry, and Medicine (Sporn, M. B., Roberts, A. B., and Goodman, D. S., eds) pp. 521–543, Raven Press, New York.
6. Mangelsdorf, D. J., Umesono, K., and Evans, R. M. (1994) in The Retinoids, Biology, Chemistry, and Medicine (Sporn, M B., Roberts, A. B., and Goodman, D. S., eds) pp. 319–350, Raven Press, New York.
7. Chambon, P. (1996) FASEB J. 10, 940–954.
8. Durster, G. (1996) Biochemistry 35, 12221–12227.
9. Napoli, J. (1996) FASEB J. 10, 993–1001.
10. Blaner, W. S., and Olson, J. A. (1994) in The Retinoids, Biology, Chemistry, and Medicine (Sporn, M. B., Roberts, A. B., and Goodman, D. S., eds) pp. 229–256, Raven Press, New York.
11. Boerman, M. H. E. M., and Napoli, J. L.(1995) Biochemistry 34, 7027–7037.
12. Boerman, M. H. E M., and Napoli, J. L. (1995) Arch. Biochem. Biophys. 321, 434–441.
13. Chai, X, Zhai, Y., Popescu, G., and Napoli, J. L. (1995) J. Biol. Chem. 270, 28408–28412.
14. Chai, X., and Napoli, J. L. (1996) Gene (Amst.) 169, 219–222.
15. Ang, H. L., Deltour, L., Hayzmizu, T. F., Zgombic-Knight, M., and Durster, G. (1996) J. Biol. Chem. 271, 9526–9534.
16. Levin, A. A., Sturzenbecker, L. J., Kazmer, S., Bosakowski, T., Huselton, C., Allenby, G., Speck, J., Kratzeisen, C. L., Rosenberger, M., Lovey, A., and Grippo, J R. (1992) Nature 355, 359–361.
17. Heyman, R. A, Mangelsdorf, D. J., Kyck, J A., Stein, R. B., Eichele, G., Evans, R. E., and Thaller, C. (1992) Cell 66, 397–406.
18. Pappas, R. S., Newcomer, M. E., and Ong, D. E (1993) Biol. Reprod. 48, 235–247.
19. Urbach, J., and Rando, R. R. (1995) Biochem. J. 299, 459–465.
20. Hebuterne, X., Wang, X.-D., Johnson, E. J., Krinsky, N. I., and Russell, R. M. (1995) J. Lipid Res. 36, 1264–1273.
21. Labrecque, J., Ehat, P. V, and Lacroix, A. (1993) Biochem. Cell Biol. 71, 85–89.
22. Labrecque, J., Dumas, F., Lacroix, A., and Bhat, P V. (1995) Biochem. J. 305, 681–684.
23. El Akawi, Z., and Napoli, J. L. (1994) Biochemistry 33, 1938–1943.
24. Maniatis, T., Fritsch, E. F., and Sambrook, J. (1982) Molecular Cloning: A Laboratory Manual, 2nd Ed., pp. 7.37–7.84, Cold Spring Harbor Laboratory, Cold Spring Harbor, N.Y.
25. Blaner, W S., Das, S. R., Gouras, P, and Flood, M. T. (1987) J. Biol. Chem. 262, 53–58.
26. Furr, H. C., Barua, A. B., and Olson, J. A. (1994) in The Retinoids, Biology,Chemistry, and Medicine (Sporn, M. B., Roberts, A. B., and Goodman, D. S.,eds) pp. 179–210, Raven Press, New York.
27. Simon, A., Hellman, U., Wernstedt, C., and Eriksson, U. (1995) J. Biol. Chem. 270, 1107–1112.
28. Driessen, C. A., Janssen, B. P., Winkens, H. J., van Bugt, A. H. de Leeuw, T. L., and Janssen, J. J. (1995) Inuest. Ophthalmol. & Visual Sci. 36,1988–1996.
29. Boleda, M. D., Saubi, N., Farres, J., and Pares, X. (1993) Arch. Biochem. Biophys. 307,85–90.
30. Takatsuka, J., Takahashi, N., and De Luca, L. M. (1996) Cancer Res. 58,675–678.

Second Series of Experiments

Recent Findings Concerning 9-cis Retinol Dehydrogenase Retinoic Acid Inhibits Human 9cRDH Activity. In order to understand whether retinoic acid can regulate 9-cis retinol dehydrogenase (9cRDH) activity, we carried out studies of the possible inhibitory effects of all-trans, 13-cis and 9-cis retinoic acid on human 9cRDH. The goal of the studies was to determine whether these retinoids regulate the activity of human 9cRDH. We were expecially interested in whether 9-cis retinoic acid, which is generated through oxidation of 9-cis retinaldehyde, the product of the 9cRDH reaction feedsback and inhibits 9cRDH activity. Indeed, as seen in Table II, these three different isomers of retinoic acid were potent inhibitors of 9cRDH activity. Especially striking is the inhibitory action of 13-cis retinoic acid. As seen in Table II, 13-cis retinoic acid inhibits 50% of 9cRDH activity when present at a concentration of 0.15 $\mu$M. This inhibitory concentration, although greater than physiologic concentrations by approximately 5-fold, is well within the range of plasma and tissue concentrations observed in humans and animal models receiving 13-cis retinoic acid for treatment of a number of clinical disorders. Both 9-cis and all-trans retinoic acid were also potent inhibitors of 9cRDH activity, although these two isomers are 15 to 30-times less potent than the 13-cis isomer. Since 13-cis retinoic acid is a far more potent inhibitor than the 9-cis and all-trans isomers, we asked whether the inhibitory effects of these isomers arises through isomerization to 13-cis retinoic acid during incubation (at 37° C. for 15 minutes) of the enzyme assay mixtures. As seen from Table III, this proved not to be the case. Although very small amounts of 13-cis retinoic acid were formed during the incubations, the concentration of 13-cis retinoic acid formed were not sufficient to account for the inhibitory actions of either all-trans or 9-cis retinoic acid.

In order to gain a better understanding of the specificity of this inhibition, we also investigated whether lipids with chemical structures similar to 13-cis retinoic acid also inhibited human 9cRDH. As shown in Table II, oleic acid, which has a cis double bond at the C-9 position of the 18 carbon fatty acid, was found to be a mild inhibitor of 9cRDH; approximately 100-fold less potent than 13-cis retinoic acid. Interestingly, the saturated fatty acid, palmitic acid, was not inhibitory towards 9cRDH. Taken together, this would suggest that a cis double bond is essential chemical feature for inhibition of human 9cRDH activity. The primary alcohols, oleyl alcohol, petroselinyl alcohol and all-trans retinol also did not inhibit 9cRDH activity. This suggests that that a carboxylic acid group is also necessary for 9cRDH inhibition.

The observation that 13-cis retinoic acid is a potent inhibitor of 9cRDH activity leads to several very important conclusions. First, since 13-cis retinoic acid is used clinically, it is possible that some of the toxicities observed in patients receiving 13-cis retinoic acid clinically may arise through the inhibition of 9cRDH activity. Considering that 13-cis retinoic acid is a poor transactivator of the retinoic acid receptors (RARs) and the retinoid X receptors (RXRs) and that it is generally assumed that 13-cis retinoic acid must be converted to all-trans retinoic acid in order to have activity, it has been difficult to understand why all of the toxicities observed for 13-cis retinoic acid do not overlap fully with those of all-trans retinoic acid. It seems possible that 13-cis retinoic acid is acting to down regulate 9cRDH activity and that this may in part account for some of the toxic actions of 13-cis retinoic acid. Since thousands of synthetic retinoids have been produced by the pharmaceutical industry, it is possible that assay of inhibitory effects on 9cRDH activity by these synthetic retinoids may serve as a rapid and useful in vitro assay for potential toxic effects in vivo by the synthetic retinoids. Secondly, considering the relatively low concentration of 13-cis retinoic acid needed to inhibit 9cRDH activity, it is also possible that 13-cis retinoic acid may play a role physiologically as a regulator of retinoic acid formation and degradation. If this working hypothesis proves correct, this may lead to the development of a new generation of drugs aimed at regulating retinoic acid formation in vivo.

Generation of Polyclonal Rabbit Antiserum Against Human 9cRDH.

In order to investigate the cellular localization of human 9cRDH in tissues, we have generated a polyclonal antiserum against a synthetic peptide corresponding to amino acid residues 237 through 256. The specific sequence of this peptide is given in Table V. The amino acid residues were selected so as to have no overlap with other members of the family of short chain alcohol dehydrogenases, including the rat liver all-trans retinol dehydrogenases and the bovine retinal pigment epithelial 11-cis retinol dehydrogenase. The antiserum generated against this peptide is able to recognize a single protein band separated by SDS-polyacrylamide gel electrophoresis. The protein band recognized by Western blot analysis with this antiserum migrates with an approximate molecular weight of 32 kDa, the expected size of human 9cRDH. It should soon be possible to use this antiserum to identify the sites of 9cRDH expression in normal and diseased human tissues. Such identification could be useful in identifying disease states that may be either responsive or refractory to retinoic acid treatment.

Cloning and Expression of the Mouse Homolog for 9cRDH. We have recently obtained full length cDNA clones for the mouse homolog for 9cRDH. Three clones were obtained independently from mouse liver, kidney and testis cDNA libraries. Each of the clones have identical coding sequences which encode a protein which shares approximately 90% identity at the amino acid level with human 9cRDH. Interestingly, as can be seen from Table IV, the 5' noncoding regions of these cDNAs are different. It is possible that these differences are important in the regulation of 9cRDH expression.

TABLE II

ESTIMATED INHIBITOR CONCENTRATION RESULTING IN 50% INHIBITION OF HUMAN 9-CIS RETINOL DEHYDROGENASE ACTIVITY (ID$_{50}$)

|  | Id$_{50}$ ($\mu$M) |
| --- | --- |
| 13-cis Retinoic Acid | 0.15 |
| 9-cis Retinoic Acid | 2.6 |
| all-trans Retinoic Acid | 4.6 |
| all-trans Retinol | >10.0 |
| Oleic Acid | 15.0 |
| Palmitic Acid | >100.0 |
| Oleyl Alcohol | >100.0 |
| Petroselinyl Alcohol | >100.0 |

TABLE III

ISOMERIZATION OF RETINOIC ACIDS IN THE HUMAN 9-CIS RETINOL DEHYDROGENASE ASSAY

| Inhibitor | all-trans | 13-cis | 9-cis |
| --- | --- | --- | --- |
| 10 $\mu$M all-trans Retinoic Acid at start: | 100% | — | — |
| all-trans Retinoic Acid at end: | 98.8% | 0.8% | 0.4% |
| 1 $\mu$M 13-cis Retinoic Acid at start: | — | 100% | — |
| 13-cis Retinoic Acid at end: | 1.6% | 98.4% | |
| 10 $\mu$M 9-cis Retinoic Acid at start: | — | — | 100% |
| 9-cis Retinoic Acid at end: | 4.2% | 1.1% | 94.7% |

TABLE IV

SEQUENCE ANALYSIS of cDNA CLONES FOR MOUSE 9-CIS RETINOL DEHYDROGENASE OBTAINED FROM LIVER, KIDNEY AND TESTIS cDNA LIBRARIES

| | | |
|---|---|---|
| Liver | (SEQ. ID NO: 6): | GCCAGTGTGCTGGAATTCGGCACGAGGCTTAGCTGTAGCTAG |
| Kidney | (SEQ. ID NO: 7): | .......................................... |
| Testis | (SEQ. ID NO: 8): | GCCCATAATCTGTTTCACACAATAAGCCATAGCTTGCCAAGCA |
| Liver: | | TGTGGGAGCCTGGGAAGTCTAGGAGCAAAGTCTCTCAAGCAGA |
| Kidney: | | .........TGGCTCNGAGGCCAAGANTCGGACCATGAGCAGA |
| Testis: | | TATAGTCTCATCTGCTCAGACCAGACATTTCCAGCTAAGTAAAT |
| Liver: | | CAGAAAGCTACAGCTTCACACATTGTGTTGCCTGCCAGCTTTCC |
| Kidney: | | CAGAAAGCTXXAGCTTCACACATTGTGTTGCCTGCCAGCTTTCC |
| Testis: | | GTTAGGGGCCAAGGCTAAAGGGGTAGAGGAAATGACAAGTTTTT |
| Liver: | | CCAGXXAGXXXXXGCTGCCCTCAGCAGGGCATCTCATCCCATC |
| Kidney: | | CCAGXXAGCCTAGGCTGCCCTCAGCAGGGCATCTCATCCCATC |
| Testis: | | CCTGCCCAGCCTAAGCTGCCCTCAGCAGGGCATCTCATCCCATC |
| Liver: | | ATGTGGCTGCCTCTGCTTCTGGGTGCCTTGCTGTGGGCAGTGCT |
| Kidney: | | ATGTGGCTGCCTCTGCTTCTGGGTGCCTTGCTGTGGGCAGTGCT |
| Testis: | | ATGTGGCTGCCTCTGCTTCTGGGTGCCTTGCTGTGGGCAGTGCT |
| Liver: | | GTGGTTGCTCAGAGACCGGCAGAGCCTGCCGGCCA................ |
| Kidney: | | GTGGTTGCTCAGAGACCGGCAGAGCCTGCCGGCCA................ |
| Testis: | | GTGGTTGCTCAGAGACCGGCAGAGCCTGCCGGCCA................ |

TABLE V

SYNTHETIC PEPTIDE USED TO GENERATE RABBIT ANTISERUM AGAINST HUMAN 9-CIS RETINOL DEHYDROGENASE

Sequence Chosen for Use in Immunization: Amino Acid Residues 237 to 256 (319 total)

Sequence(SEQ. ID NO: 9): HYGGAFLKYLKMQQRIMNLI

---

What is claimed is:

1. An isolated human 9-cis-retinol dehydrogenase encoded by the isolated nucleic acid molecule whose sequence is set forth in FIG. 1A (SEO ID NO:1).

2. The 9-cis-retinol dehydrogenase of claim 1, wherein the 9-cis-retinol dehydrogenase comprises the amino acid sequence as shown in FIG. 1B (SEQ. ID NO: 2).

3. An isolated mouse 9-cis-retinol dehydrogenase, wherein the nucleic acid molecule encoding the 9-cis-retinol dehydrogenase comprises the nucleotide sequence shown in any of SEQ. ID NOS: 6, 7, and 8.

* * * * *

SEQUENCE LISTING

<160> NUMBER OF SEQ ID NOS: 13

<210> SEQ ID NO 1
<211> LENGTH: 1230
<212> TYPE: DNA
<213> ORGANISM: human
<220> FEATURE:
<223> OTHER INFORMATION: n= unknown

<400> SEQUENCE: 1

```
gagactggga gcagtctctt aaacaaaagc aaaagaataa gcttcgggcg ctgtagtacc      60
tgccagcttt cgccacagga ggctgccacc tgtaggtcac ttgggctcca gctatgtggc     120
tgcctcttct gctgggtgcc ttactctggg cagtgctgtg gttgctcagg gaccggcaga     180
```

-continued

```
ncctgcccgc cagcaatgcc tttgtcttca tcaccggctg tgactcaggc tttgggcgcc      240
ttctggcact gcagctggac cagaaaagct tccgantcct ggccagctgc ctgaccccct      300
ccggggcgga ggacctgcag ggggtggctt cttccggctt caacaccacc ntgttggata      360
tcactgatcc ccagagcttc agcaggcag  ccaagtgggt ggagatgcac gttaaggaag      420
cagggctttt tggtctggtg aataatgctg gtgtggctgg tatcatcgga cccacaccat      480
ggctgacccg ggacgatttc agcgggtgc  tgaatgtgaa cacaatgggt cccatcgggg      540
tcacccttgc cctgctgcct ctgctgcagc aagcccgggg ccgggtgatc aacatcacca      600
gcgtcctggg tcgcctggca gccaatggtg ggggctactg tgtctccaaa tttggcctgg      660
aggccttctc tgacagcctg aggcgggatg tagctcattt tgggatacgg gagtccatng      720
tggagcctgg tttnttccga accctgtga  ccaacttgga gagtntggag aaaaccctgc      780
aggcctgctg ggcacggctg cctcctgcca cacaggccca ctatgggggg gccttcctca      840
ccaagtacct gaaaatgcaa cagcgcatca tgaacctgat ctgtgacccg gacctaacca      900
aggtgagcca tgcctggag  catgcccctga ctgctcgaca ccccgaacc  cgctacagcc      960 caggttggga tgccaagctg ctctggctgc ctgcctccta cctgccagcc agcctggtgg     1020
atgctgtgct cacctgggtc cttcccaagc ctgcccaagc agtctactga atccagcctt     1080
ccagcaagag attgttttc  aaggacaagg actttgattt atttctgccc ccaccctggt     1140
actgcctggt gcctgccaca aaataagcac taacaaaagt gtattgttta aaaaataaaa     1200
agaaggtggg cagaaatgtg cccagtggaa                                      1230
```

<210> SEQ ID NO 2
<211> LENGTH: 318
<212> TYPE: PRT
<213> ORGANISM: human
<220> FEATURE:
<223> OTHER INFORMATION: Xaa = unknown

<400> SEQUENCE: 2

```
Met Trp Leu Pro Leu Leu Leu Gly Ala Leu Leu Trp Ala Val Leu Trp
  1               5                  10                  15

Leu Leu Arg Asp Arg Gln Xaa Leu Pro Ala Ser Asn Ala Phe Val Phe
             20                  25                  30

Ile Thr Gly Cys Asp Ser Gly Phe Gly Arg Leu Leu Ala Leu Gln Leu
         35                  40                  45

Asp Gln Lys Ser Phe Arg Xaa Leu Ala Ser Cys Leu Thr Pro Ser Gly
     50                  55                  60

Ala Glu Asp Leu Gln Gly Val Ala Ser Ser Gly Phe Asn Thr Thr Xaa
 65                  70                  75                  80

Leu Asp Ile Thr Asp Pro Gln Ser Phe Gln Gln Ala Ala Lys Trp Val
                 85                  90                  95

Glu Met His Val Lys Glu Ala Gly Leu Phe Gly Leu Val Asn Asn Ala
            100                 105                 110

Gly Val Ala Gly Ile Ile Gly Pro Thr Pro Trp Leu Thr Arg Asp Asp
        115                 120                 125

Phe Gln Arg Val Leu Asn Val Asn Thr Met Gly Pro Ile Gly Val Thr
    130                 135                 140

Leu Ala Leu Leu Pro Leu Leu Gln Gln Ala Arg Gly Arg Val Ile Asn
145                 150                 155                 160

Ile Thr Ser Val Leu Gly Arg Leu Ala Ala Asn Gly Gly Gly Tyr Cys
                165                 170                 175
```

```
Gly Ser Lys Phe Gly Leu Glu Ala Phe Ser Asp Ser Leu Arg Arg Asp
            180                 185                 190

Val Ala His Phe Gly Ile Arg Glu Ser Xaa Val Glu Pro Gly Xaa Phe
            195                 200                 205

Arg Thr Pro Val Thr Asn Leu Glu Ser Xaa Glu Lys Thr Leu Gln Ala
            210                 215                 220

Cys Trp Ala Arg Leu Pro Pro Ala Thr Gln Ala His Tyr Gly Gly Ala
225                 230                 235                 240

Phe Leu Thr Lys Tyr Leu Lys Met Gln Gln Arg Ile Met Asn Leu Ile
            245                 250                 255

Cys Asp Pro Asp Leu Thr Lys Val Ser Arg Cys Leu Glu His Ala Leu
            260                 265                 270

Thr Ala Arg His Pro Arg Thr Arg Tyr Ser Pro Gly Trp Asp Ala Lys
            275                 280                 285

Leu Leu Trp Leu Pro Ala Ser Tyr Leu Pro Ala Ser Leu Val Asp Ala
            290                 295                 300

Val Leu Thr Trp Val Leu Pro Lys Pro Ala Gln Ala Val Tyr
305                 310                 315

<210> SEQ ID NO 3
<211> LENGTH: 318
<212> TYPE: PRT
<213> ORGANISM: rat

<400> SEQUENCE: 3

Met Trp Leu Pro Leu Leu Leu Gly Val Leu Leu Trp Ala Ala Leu Trp
1               5                   10                  15

Leu Leu Arg Asp Arg Gln Cys Leu Pro Ala Ser Asp Ala Phe Ile Phe
            20                  25                  30

Ile Thr Gly Cys Asp Ser Gly Phe Gly Arg Leu Leu Ala Leu Arg Leu
            35                  40                  45

Asp Gln Arg Gly Phe Arg Val Leu Ala Ser Cys Leu Thr Pro Ser Gly
        50                  55                  60

Ala Glu Asp Leu Gln Arg Val Ala Ser Ser Arg Leu His Thr Thr Leu
65                  70                  75                  80

Leu Asp Val Thr Asp Pro Gln Ser Ile Arg Gln Ala Val Lys Trp Val
                85                  90                  95

Glu Thr His Val Gly Glu Ala Gly Leu Phe Gly Leu Val Asn Asn Ala
            100                 105                 110

Gly Val Ala Gly Ile Ile Gly Pro Thr Pro Trp Gln Thr Arg Glu Asp
            115                 120                 125

Phe Gln Arg Val Leu Asn Val Asn Thr Leu Gly Pro Ile Gly Val Thr
        130                 135                 140

Leu Ala Leu Leu Pro Leu Leu Gln Ala Arg Gly Arg Val Ile Asn Asn
145                 150                 155                 160

Ile Thr Ser Val Leu Gly Arg Leu Ala Ala Asn Gly Gly Gly Tyr Cys
                165                 170                 175

Val Ser Lys Phe Gly Leu Glu Ala Phe Ser Asp Ser Leu Arg Arg Asp
            180                 185                 190

Val Ala Pro Phe Gly Val Arg Val Ser Ile Val Glu Pro Gly Phe Phe
            195                 200                 205

Arg Thr Pro Val Thr Asn Leu Glu Thr Leu Glu Asp Thr Leu Gln Ala
            210                 215                 220

Cys Trp Ala Arg Leu Pro Pro Ala Thr Gln Ala Leu Tyr Gly Glu Ala
```

```
225                 230                 235                 240
Phe Leu Thr Lys Tyr Leu Arg Val Gln Gln Arg Ile Met Asn Met Ile
                245                 250                 255

Cys Asp Pro Asp Leu Ala Lys Val Ser Arg Cys Leu Glu His Ala Leu
            260                 265                 270

Thr Ala Arg His Pro Arg Thr Arg Tyr Ser Pro Gly Trp Asp Ala Lys
        275                 280                 285

Leu Leu Trp Leu Pro Ala Ser Tyr Leu Pro Ala Arg Leu Val Asp Ala
    290                 295                 300

Val Leu Ala Trp Val Leu Pro Lys Pro Ala Gln Thr Val Tyr
305                 310                 315
```

<210> SEQ ID NO 4
<211> LENGTH: 317
<212> TYPE: PRT
<213> ORGANISM: rat

<400> SEQUENCE: 4

```
Met Trp Leu Tyr Leu Leu Ala Leu Val Gly Leu Trp Asn Leu Leu Arg
  1               5                  10                  15

Leu Phe Arg Glu Arg Lys Val Val Ser His Leu Gln Asp Lys Tyr Val
                20                  25                  30

Phe Ile Thr Gly Cys Asp Ser Gly Phe Gly Asn Leu Leu Ala Arg Gln
            35                  40                  45

Leu Asp Arg Arg Gly Met Arg Val Leu Ala Ala Cys Leu Thr Glu Lys
        50                  55                  60

Gly Ala Glu Gln Leu Arg Ser Lys Thr Ser Asp Arg Leu Glu Thr Val
 65                  70                  75                  80

Ile Leu Asp Val Thr Lys Thr Glu Ser Ile Val Ala Ala Thr Gln Trp
                85                  90                  95

Val Lys Glu Arg Val Gly Asn Thr Gly Leu Trp Gly Leu Val Asn Asn
            100                 105                 110

Ala Gly Ile Ser Gly His Leu Gly Pro Asn Glu Trp Met Asn Lys Gln
        115                 120                 125

Asn Ile Ala Ser Val Leu Asp Val Asn Leu Leu Gly Met Ile Glu Val
    130                 135                 140

Thr Leu Ser Thr Val Pro Leu Val Arg Lys Ala Arg Gly Arg Val Val
145                 150                 155                 160

Asn Val Ala Ser Ile Ala Gly Arg Leu Ser Phe Cys Gly Gly Gly Tyr
                165                 170                 175

Cys Ile Ser Lys Tyr Gly Val Glu Ala Phe Ser Asp Ser Leu Arg Arg
            180                 185                 190

Glu Leu Ser Tyr Phe Gly Val Lys Val Ala Ile Val Glu Pro Gly Phe
        195                 200                 205

Phe Arg Thr Asp Val Thr Asn Gly Val Thr Leu Ser Ser Asn Phe Gln
    210                 215                 220

Met Leu Trp Asp Gln Thr Ser Ser Glu Val Arg Glu Val Tyr Gly Glu
225                 230                 235                 240

Asn Tyr Leu Ala Ser Tyr Leu Lys Met Leu Asn Gly Leu Asp Gln Arg
                245                 250                 255

Cys Asn Lys Asp Leu Ser Leu Val Thr Asp Cys Met Glu His Ala Leu
            260                 265                 270

Thr Ser Cys His Pro Arg Thr Arg Tyr Ser Ala Gly Trp Asp Ala Lys
        275                 280                 285
```

```
Phe Phe Tyr Leu Pro Met Ser Tyr Leu Pro Thr Phe Leu Val Asp Ala
    290                 295                 300

Leu Phe Tyr Trp Thr Ser Pro Lys Pro Glu Lys Ala Leu
305                 310                 315
```

<210> SEQ ID NO 5
<211> LENGTH: 317
<212> TYPE: PRT
<213> ORGANISM: Bovine

<400> SEQUENCE: 5

```
Met Trp Leu Tyr Leu Leu Ala Leu Val Gly Leu Trp Asn Leu Leu Arg
  1               5                  10                  15

Phe Leu Arg Glu Arg Lys Val Val Ser His Leu Gln Asp Lys Tyr Val
             20                  25                  30

Phe Ile Thr Gly Cys Asp Ser Gly Phe Gly Asn Leu Leu Ala Arg Gln
         35                  40                  45

Leu Asp Arg Arg Gly Met Arg Val Leu Ala Ala Cys Leu Thr Glu Lys
     50                  55                  60

Gly Ala Glu Gln Leu Arg Ser Lys Thr Ser Asp Arg Leu Glu Thr Val
 65                  70                  75                  80

Ile Leu Asp Val Thr Lys Thr Glu Ser Ile Val Ala Ala Thr Gln Trp
                 85                  90                  95

Val Lys Glu Arg Val Gly Asn Arg Gly Leu Trp Gly Leu Val Asn Asn
            100                 105                 110

Ala Gly Ile Ser Val Pro Val Gly Pro Asn Glu Trp Met Arg Lys Lys
        115                 120                 125

Asp Phe Ala Ser Val Leu Asp Val Asn Leu Leu Gly Val Ile Glu Val
    130                 135                 140

Thr Leu Asn Met Leu Pro Leu Val Arg Lys Ala Arg Gly Arg Val Val
145                 150                 155                 160

Asn Ile Ala Ser Thr Met Gly Arg Met Ser Leu Val Gly Gly Gly Tyr
                165                 170                 175

Cys Ile Ser Lys Tyr Gly Val Glu Ala Phe Ser Asp Ser Leu Arg Arg
            180                 185                 190

Glu Leu Thr Tyr Phe Gly Val Lys Val Ala Ile Ile Glu Pro Gly Gly
        195                 200                 205

Phe Lys Thr Asn Val Thr Asn Met Glu Arg Leu Ser Asp Asn Leu Lys
    210                 215                 220

Lys Leu Trp Asp Gln Thr Thr Glu Glu Val Lys Glu Ile Tyr Gly Glu
225                 230                 235                 240

Lys Phe Gln Asp Ser Tyr Met Lys Ala Met Glu Ser Leu Val Asn Thr
                245                 250                 255

Cys Ser Gly Asp Leu Ser Leu Val Thr Asp Cys Met Glu His Ala Leu
            260                 265                 270

Thr Ser Cys His Pro Arg Thr Arg Tyr Ser Pro Gly Trp Asp Ala Lys
        275                 280                 285

Phe Phe Tyr Leu Pro Met Ser Tyr Leu Pro Thr Phe Leu Ser Asp Ala
    290                 295                 300

Val Ile His Trp Gly Ser Val Lys Pro Ala Arg Ala Leu
305                 310                 315
```

<210> SEQ ID NO 6
<211> LENGTH: 252
<212> TYPE: DNA
<213> ORGANISM: mouse

<220> FEATURE:
<223> OTHER INFORMATION: n= unknown

<400> SEQUENCE: 6

| cgccagtgtg | ctggaattcg | gcacgaggct | tagctgtagc | tagtgtggga | gcctgggaag | 60 |
| tctaggagca | aagtctctca | agcagacaga | aagctacagc | ttcacacatt | gtgttgcctg | 120 |
| ccagctttcc | ccagnnagnn | nnngctgccc | tcagcaggga | atctcatccc | atcatgtggc | 180 |
| tgcctctgct | tctgggtgcc | ttgctgtggg | cagtgctgtg | gttgctcaga | gaccggcaga | 240 |
| gcctgccggc | ca | | | | | 252 |

<210> SEQ ID NO 7
<211> LENGTH: 200
<212> TYPE: DNA
<213> ORGANISM: mouse
<220> FEATURE:
<223> OTHER INFORMATION: n= unknown

<400> SEQUENCE: 7

| tggctcngag | gccaagantc | ggaccatgag | cagacagaaa | gctnnagctt | cacacattgt | 60 |
| gttgcctgcc | agctttcccc | agnnagccta | ggctgccctc | agcagggcat | ctcatcccat | 120 |
| catgtggctg | cctctgcttc | tgggtgcctt | gctgtgggca | gtgctgtggt | tgctcagaga | 180 |
| ccggcagagc | ctgccggcca | | | | | 200 |

<210> SEQ ID NO 8
<211> LENGTH: 254
<212> TYPE: DNA
<213> ORGANISM: mouse

<400> SEQUENCE: 8

| tgcccataat | ctgtttcaca | caataagcca | tagcttgcca | agcatatagt | ctcatctgct | 60 |
| cagaccagac | atttccagct | aagtaaatgt | taggggccaa | ggctaaaggg | gtagaggaaa | 120 |
| tgacaagttt | tcctgcccag | cctaagctgc | cctcagcagg | gcatctcatc | ccatcatgtg | 180 |
| gctgcctctg | cttctgggtg | ccttgctgtg | ggcagtgctg | tggttgctca | gagaccggca | 240 |
| gagcctgccg | gcca | | | | | 254 |

<210> SEQ ID NO 9
<211> LENGTH: 20
<212> TYPE: PRT
<213> ORGANISM: human

<400> SEQUENCE: 9

His Tyr Gly Gly Ala Phe Leu Lys Tyr Leu Lys Met Gln Gln Arg Ile
 1               5                  10                  15
Met Asn Leu Ile
            20

<210> SEQ ID NO 10
<211> LENGTH: 1229
<212> TYPE: DNA
<213> ORGANISM: mouse

<400> SEQUENCE: 10

| tacgggctcg | agccagacg | ccgttgctat | tcggacagct | tccatagttg | agctgaacta | 60 |
| gaagtctcag | cagacagaaa | gctacagctt | cacacattgt | gttgcctgcc | agctttcccc | 120 |
| agagcctagc | tgccctcagc | agggcatctc | atcccatcat | gtggctgcct | ctgcttctgg | 180 |

| | |
|---|---|
| gtgccttgct gtgggcagtg ctgtggttgc tcagagaccg gcagagcctg ccggccagtg | 240 |
| atgctttcat cttcatcact ggctgtgact ctggctttgg gcgccttctg gcactgcaac | 300 |
| ttgaccagaa gggcttccaa gtcctggccg gctgcctgac ccctctggga gcagaagacc | 360 |
| tgcagcagat ggcctcctcc cgcctccaca caacactact ggatatcact gatccccaga | 420 |
| atgtccagca agttgccaag tgggtgaaga cacgtgttgg agaaactgga cttttggtc | 480 |
| tggtgaataa cgctggcgta gctggtatca tcgggcccac accatggcta acacaggatg | 540 |
| atttccagag agtactgagt gtgaacacac tgggcccat cggtgtcacc cttgccctgc | 600 |
| tgcccctgct acagcaggcc aggggtcggg tggtcaacat caccagtgtc ttgggccgca | 660 |
| tagcagccaa tggcgggggc tactgtgtct ccaagtttgg cctggaggcc ttctctgaca | 720 |
| gcctgaggcg ggacatggct ccgttcggag tacaagtctc cattgtggag cctggcttct | 780 |
| ttcgaacccc tgtgaccaac ctggagagtc tggagagcac cctgaaggct tgttgggccc | 840 |
| ggctacctcc agctatacag gcccactacg gggaagcctt cctcgatact tatcttcgag | 900 |
| tacagcgccg catcatgaac ctgatctgtg acccagaact aacgaaggtg accagctgcc | 960 |
| tggagcatgc ctgactgctc gccaccccg aacacgtaca gcccaggctg ggatgccaag | 1020 |
| ctgctctggc tgcctgcctc ctaccttcca gccagggtgg tggatgctgt gctcactgga | 1080 |
| tccttccccg gcccgcccag tcagtctcct gattccagct ttacagcaag agctgatttt | 1140 |
| gaaaagcaag gcatctattt ctgtgtctac ccagtgctgc ctggtttctg ataccaatta | 1200 |
| gctctcaata aatatttgct ttaatcaaa | 1229 |

<210> SEQ ID NO 11
<211> LENGTH: 461
<212> TYPE: DNA
<213> ORGANISM: mouse

<400> SEQUENCE: 11

| | |
|---|---|
| tggctcngag gccaagantc ggaccatgag cagacagaaa gctacagctt cacacattgt | 60 |
| gttgcctgcc agctttcccc agagcctagg ctgccctcag cagggcatct catcccatca | 120 |
| tgtggctgcc tctgcttctg ggtgccttgc tgtgggcagt gctgtggttg ctcagagacc | 180 |
| ggcagagcct gccggccagt gatgctttca tcttcatcac tggctgtgac tctggctttg | 240 |
| gcgccttct ggcactgcaa cttgaccaga agggcttcca agtcctggcc ggctgcctga | 300 |
| ccccctctgg agcagaagac ctgcagcaga tggcctcctc ccgcctccac acaacaccac | 360 |
| tggatatcac tgatccccag aatgtccagc aagttgccaa gtgggtgaag cacgtgttg | 420 |
| gagaaactgg acttttggt ctggtgaata acgctggcgt a | 461 |

<210> SEQ ID NO 12
<211> LENGTH: 1278
<212> TYPE: DNA
<213> ORGANISM: mouse

<400> SEQUENCE: 12

| | |
|---|---|
| cttggtaccg agctcgganc cactagtaac ggccgccagt gtgctggaat tcggcacgag | 60 |
| gcttagctgt agctagtgtg ggagcctggg aagtctagga gcaaagtctc tcaagcagac | 120 |
| agaaagctac agcttcacac attgtgttgc ctgccagctt tccccagagg ctgccctcag | 180 |
| cagggcatct catcccatca tgtggctgcc tctgcttctg ggtgccttgc tgtgggcagt | 240 |
| gctgtggttg ctcagagacc ggcagagcct gccggccagt gatgctttca tcttcatcac | 300 |
| tggctgtgac tctggctttg gcgccttct ggcactgcaa cttgaccaga agggcttcca | 360 |

-continued

```
agtcctggcc ggctgcctga cccctctgg agcagaagac ctgcagcaga tggcctcctc      420
ccgcctccac acaacactac tggatatcac tgatccccag aatgtccagc aagttgccaa      480
gtgggtgaag acacgtgttg agaaactgg acttttggt ctggtgaata acgctggcgt       540
agctggtatc atcgggccca caccatggct aacacaggat gatttccaga gagtactgag     600
tgtgaacaca ctggggccca tcggtgtcac ccttgccctg ctgccctgc tacagcaggc      660 cagggtcgg gtggtcaaca tcaccagtgt cttgggccgc atagcagcca atggcggggg     720
ctactgtgtc tccaagtttg gcctggaggc cttctctgac agcctgaggc gggacatggc    780
tccgttcgga gtacaagtct ccattgtgga gcctggcttc tttcgaaccc ctgtgaccaa    840
cctggagagt ctggagagca ccctgaaggc ttgttgggcc cggctacctc cagctataca    900
ggcccactac ggggaagcct tcctcgatac ttatcttcga gtacagcgcc gcatcatgaa    960
cctgatctgt gacccagaac taacgaaggt gaccagctgc ctggagcatg ccctgactgc   1020
tcgccacccc cgaacacgct acagcccagg ctgggatgcc aagctgctct ggctgcctgc   1080
ctcctacctt ccagccaggg tggtggatgc tgtgctcacc tggatccttc ccggccgc     1140 ccagtcagtc tcctgattcc agctttacag caagaagctg attttgaaaa gcaaggcatc   1200
tatttctgtg tctacccagt gctgcctggt ttctgatacc aattangctc tcaataaata   1260
tntntgcttt naatcaaa                                                 1278
```

<210> SEQ ID NO 13
<211> LENGTH: 1334
<212> TYPE: DNA
<213> ORGANISM: mouse

<400> SEQUENCE: 13

```
gagtcacaca gggataggtc tgcccacagg accagctcag gtttatttca ttagctacaa      60
agtgcttgcc cataatctgt ttcacacaat aagccatagc ttgccaatcc tctgccaagc     120
atatagtctc atctgctcag accagacatt tccagctaag taaatgttag gggccaaggc    180
taaaggggta gaggaaatga caagttttcc tgcccagcct aagctgccct cagcagggca    240
tctcatccca tcatgtggct gcctctgctt ctgggtgcct tgctgtgggc agtgctgtgg    300
ttgctcagag accggcagag cctgccggcc agtgatgctt tcatcttcat cactggctgt    360
gactctggct ttgggcgcct tctggcactg caacttgacc agaagggctt ccaagtcctg    420
gccggctgcc tgaccccctc tggagcagaa gacctgcagc agatggcctc ctcccgcctc    480
cacacaacac tactggatat cactgatccc cagaatgtcc agcaagttgc caagtgggtg    540
aagacacgtg ttggagaaac tggacttttt ggtctggtga ataacgctgg cgtagctggt    600
atcatcgggc ccacaccatg gctaacacag gatgatttcc agagagtact gagtgtgaac    660
acactggggc ccatcggtgt cacccttgcc ctgctgcccc tgctacagca ggccaggggt    720
cgggtggtca acatcaccag tgtcttgggc cgcatagcag ccaatggcgg gggctactgt    780
gtctccaagt ttggcctgga ggccttctct gacagcctga gcgggacat ggctccgttc    840 ggagtacaag tctccattgt ggagcctggc ttctttcgaa cccctgtgac caacctggag    900
agtctggaga gcaccctgaa ggcttgttgg gcccggctac ctccagctat acaggcccac    960
tacggggaag ccttcctcga tacttatctt cgagtacagc gccgcatcat gaacctgatc   1020
tgtgacccag aactaacgaa ggtgaccagc tgcctggagc atgccgtgac tgctcgccac   1080
ccccgaacac gttacagccc aggctgggat gccaagctgc tctggctgcc tgcctcctac   1140
```

```
cttccagcca gggtggtgga tgctgtgctc acatggatcc ttccccggcc cgcccagtca    1200
gtctcctgat tccagcttta cagcaagagg ctgattttga aaagcaaggc atctatttct    1260
gtgtctaccc agtgctgcct ggtttctgat accaattagg ctctcaataa atatgtattg    1320
ctttaaatca aaaa                                                      1334
```